US012642443B2

(12) United States Patent
Rabinovich et al.

(10) Patent No.: US 12,642,443 B2
(45) Date of Patent: Jun. 2, 2026

(54) SYSTEM AND METHOD FOR PROVIDING USER FEEDBACK OF BLOOD PRESSURE SENSOR PLACEMENT AND CONTACT QUALITY

(71) Applicant: LiveMetric (Medical) S.A., Luxembourg (LU)

(72) Inventors: Adi Efraim Joseph Rabinovich, Netanya (IL); Nir Efraim Joseph Tal, Haifa (IL); Tomer Bentzion, Tel Aviv (IL); Ori Hay, Aviel (IL)

(73) Assignee: LiveMetric (Medical) S.A., Luxembourg (LU)

( * ) Notice: Subject to any disclaimer, the term of this patent is extended or adjusted under 35 U.S.C. 154(b) by 523 days.

(21) Appl. No.: 15/847,595

(22) Filed: Dec. 19, 2017

(65) Prior Publication Data

US 2018/0184920 A1 Jul. 5, 2018

Related U.S. Application Data

(60) Provisional application No. 62/442,917, filed on Jan. 5, 2017.

(51) Int. Cl.
| | |
|---|---|
| *A61B 5/021* | (2006.01) |
| *A61B 5/00* | (2006.01) |
| (Continued) | |

(52) U.S. Cl.
CPC ........ *A61B 5/02108* (2013.01); *A61B 5/0205* (2013.01); *A61B 5/02416* (2013.01);
(Continued)

(58) Field of Classification Search
None
See application file for complete search history.

(56) References Cited

U.S. PATENT DOCUMENTS

| | | | |
|---|---|---|---|
| 4,605,010 | A | 8/1986 | Mcewen |
| 5,243,992 | A | 9/1993 | Eckerle et al. |
| | | (Continued) | |

FOREIGN PATENT DOCUMENTS

| | | |
|---|---|---|
| CN | 102564470 A | 7/2012 |
| CN | 102613966 A | 8/2012 |
| | (Continued) | |

OTHER PUBLICATIONS

Yousefi et al., "Adaptive Cancellation of Motion Artifacts in Waerable Biosensors", 34 Conf. IEEE EMBS, pp. 2004-2208, Aug. 28, 2012.

(Continued)

*Primary Examiner* — Jacqueline Cheng
*Assistant Examiner* — Jairo H Portillo
(74) *Attorney, Agent, or Firm* — The Roy Gross Law Firm, LLC; Roy D. Gross

(57) ABSTRACT

A novel and useful system and method for generating user feedback related to the quality of the placement and contact of a blood pressure sensor on a user's body. The sensor is incorporated in a wearable blood pressure measurement device that is capable of analyzing and providing feedback regarding the quality of placement and contact of the pressure sensor array. The wearable includes a pressure sensor array for monitoring blood pressure, means for attaching the pressure sensor to a user's body for measuring a region, a processor operative to record pressure signals from said sensor array and to calculate quality of pressure sensor contact to measurement area score, and a display operative to determine and display the quality of the placement and contact of the pressure sensor. A quality metric indicating the quality of the placement and contact of the pressure sensor is provided as feedback to the user. Directional arrows along
(Continued)

USER FEEDBACK METHOD

RECEIVE DATA FROM EACH SENSOR ELEMENT IN SENSOR ARRAY — 290

PERFORM PULSE ANALYSIS ON OUTPUT FROM EACH SENSOR ELEMENT — 292

CALCULATE QUALITY METRIC FOR EACH SENSOR ELEMENT — 294

GENERATE SPATIAL MAP OF QUALITY METRICS FOR THE SENSOR ARRAY — 296

PROVIDE FEEDBACK TO THE USER IN ACCORDANCE WITH THE SPATIAL MAP OF METRICS — 298

PROVIDE PLACEMENT FEEDBACK TO THE USER AS THE USER ADJUSTS POSITIONING OF THE SENSOR ARRAY ON THEIR PERSON — 300

END with alphanumeric messages guide the user to achieve optimum placement of the device.

19 Claims, 15 Drawing Sheets

(51) Int. Cl.
    *A61B 5/0205*      (2006.01)
    *A61B 5/024*       (2006.01)
    *A61B 5/0295*      (2006.01)
(52) U.S. Cl.
    CPC ........ *A61B 5/02438* (2013.01); *A61B 5/0295* (2013.01); *A61B 5/681* (2013.01); *A61B 5/746* (2013.01); *A61B 5/7207* (2013.01); *A61B 5/7264* (2013.01)

(56)                    References Cited

U.S. PATENT DOCUMENTS

| | | | |
|---|---|---|---|
| 7,395,105 | B2 | 7/2008 | Schmidt et al. |
| 7,438,687 | B2 | 10/2008 | Lewicke |
| 7,539,532 | B2 | 5/2009 | Tran |
| 7,641,614 | B2 | 1/2010 | Asada et al. |
| 8,747,327 | B2 | 6/2014 | Kim et al. |
| 9,149,230 | B2 | 10/2015 | Caron et al. |
| 9,398,880 | B2 | 7/2016 | Barnett |
| 9,504,392 | B2 | 11/2016 | Caron et al. |
| 2003/0065269 | A1* | 4/2003 | Vetter .................... A61B 5/721 |
| | | | 600/503 |
| 2006/0036185 | A1 | 2/2006 | Lewicke et al. |
| 2007/0055163 | A1 | 3/2007 | Asada et al. |
| 2007/0265533 | A1 | 11/2007 | Tran |
| 2008/0091113 | A1 | 4/2008 | Kondo et al. |
| 2008/0228089 | A1 | 9/2008 | Cho et al. |
| 2009/0151475 | A1 | 6/2009 | Masaki et al. |
| 2010/0286538 | A1 | 11/2010 | Kim et al. |
| 2010/0298895 | A1* | 11/2010 | Ghaffari ................. A61B 18/14 |
| | | | 607/3 |
| 2011/0112379 | A1* | 5/2011 | Li ...................... A61B 5/14551 |
| | | | 600/300 |
| 2011/0152700 | A1 | 6/2011 | Sawanoi et al. |
| 2011/0166461 | A1 | 7/2011 | Susstrunk et al. |
| 2012/0316448 | A1 | 12/2012 | Gu et al. |
| 2013/0144176 | A1* | 6/2013 | Lec .................... A61B 5/02233 |
| | | | 600/485 |
| 2013/0275057 | A1 | 10/2013 | Perlin et al. |
| 2014/0081160 | A1* | 3/2014 | Xiang ................ A61B 5/02444 |
| | | | 600/500 |
| 2014/0180152 | A1* | 6/2014 | Maskara .............. A61B 5/0422 |
| | | | 600/523 |
| 2014/0243709 | A1 | 8/2014 | Gibson et al. |
| 2014/0249386 | A1 | 9/2014 | Caron et al. |
| 2014/0288383 | A1 | 9/2014 | Barnett |
| 2014/0288443 | A1 | 9/2014 | Meriheina et al. |
| 2014/0288445 | A1 | 9/2014 | Makkonen et al. |
| 2014/0330145 | A1* | 11/2014 | Brodnick ........... A61B 5/04012 |
| | | | 600/509 |
| 2014/0358012 | A1 | 12/2014 | Richards et al. |
| 2015/0366518 | A1 | 12/2015 | Sampson |
| 2015/0370398 | A1 | 12/2015 | Perlin et al. |
| 2016/0066894 | A1 | 3/2016 | Barton-sweeney |
| 2016/0094899 | A1* | 3/2016 | Aumer ................... G08B 21/18 |
| | | | 340/870.07 |
| 2016/0113517 | A1* | 4/2016 | Lee ...................... G01J 5/0859 |
| | | | 600/474 |
| 2016/0262695 | A1 | 9/2016 | Zhang et al. |
| 2016/0278645 | A1 | 9/2016 | Yoon |
| 2016/0287110 | A1* | 10/2016 | Morris ............... A61B 5/02416 |
| 2016/0367158 | A1* | 12/2016 | Samadani .......... A61B 5/02438 |
| 2016/0367406 | A1 | 12/2016 | Barnett |
| 2017/0135640 | A1* | 5/2017 | Gunasekar ........... A61B 5/6843 |
| 2017/0172431 | A1 | 6/2017 | Kim et al. |
| 2017/0224226 | A1 | 8/2017 | Kitagawa et al. |
| 2017/0360306 | A1 | 12/2017 | Narasimhan et al. |
| 2018/0263517 | A1 | 9/2018 | Kubo |
| 2018/0325454 | A1 | 11/2018 | Petelenz et al. |
| 2019/0380624 | A1 | 12/2019 | Ota et al. |

FOREIGN PATENT DOCUMENTS

| | | |
|---|---|---|
| JP | 357168183 | 10/1982 |
| JP | S57168183 A | 10/1982 |
| JP | 3029912 B2 | 4/2000 |
| JP | 2008-168032 A | 7/2008 |
| JP | 2008-245943 A | 10/2008 |
| JP | 2011239840 | 12/2011 |
| JP | 2014-168675 A | 9/2014 |
| JP | 2015501184 | 1/2015 |
| JP | 5561674 B2 | 7/2017 |
| KR | 10-2016-0105481 | 9/2016 |
| WO | WO 2005/094672 A1 | 10/2005 |
| WO | WO 2006/020956 A2 | 2/2006 |
| WO | WO 2006/094107 A1 | 9/2006 |
| WO | WO 2007/024777 A2 | 3/2007 |
| WO | 2008118874 A2 | 10/2008 |
| WO | WO 2009/125349 A2 | 10/2009 |
| WO | WO 2013/061281 A1 | 5/2013 |
| WO | WO 2014/153399 A1 | 9/2014 |
| WO | 2015103061 | 7/2015 |
| WO | WO 2015/107269 A1 | 7/2015 |
| WO | WO 2015/143259 A1 | 9/2015 |
| WO | WO 2015/172897 A1 | 11/2015 |
| WO | WO 2015/183470 A9 | 12/2015 |
| WO | WO 2016/040253 A1 | 3/2016 |
| WO | WO 2016/040256 A1 | 3/2016 |
| WO | WO 2016/041073 A1 | 3/2016 |
| WO | WO 2016/061668 A1 | 4/2016 |
| WO | 2016067866 A1 | 5/2016 |
| WO | WO 2016/065463 A1 | 5/2016 |
| WO | WO 2016/065476 A1 | 5/2016 |
| WO | WO 2016/161227 A2 | 10/2016 |
| WO | WO 2017/074713 A1 | 5/2017 |
| WO | WO 2018/081208 A1 | 5/2018 |

OTHER PUBLICATIONS

Valle-Lopera et al., "Test and fabrication of piezoresistive sensors for contact pressure measurement", Revista Facultad de Ingeniería, Univ Antigua, No. 82, pp. 47-52, 2017.

International Search Report issued in PCT/US2016/056958 issued Jan. 26, 2017.

International Search Report issued in PCT/US2017/058197 issued Mar. 1, 2018.

International Search Report issued in PCT/US2017/058419 issued Apr. 12, 2018.

International Search Report issued in PCT/US2017/058420 issued Apr. 12, 2018.

Written Opinion issued in PCT/US2016/056958 issued Jan. 26, 2017.

Written Opinion issued in PCT/US2017/058197 issued Mar. 1, 2018.

Written Opinion issued in PCT/US2017/058419 issued Apr. 12, 2018.

Written Opinion issued in PCT/US2017/058420 issued Apr. 12, 2018.

Connell et al., "Continuous Wearable Blood Pressure Monitor", Medical Design Briefs, p. 22, Nov. 2016.

Aditya et al (2015) Novel Applications of Force Sensing Resistors in Healthcare Technologies, Proceedings of Healthy World Conference.

Aditya et al (2015) Real Time Monitoring of Arterial Pulse Waveform Parameters Using Low Cost, Non-invasive force transducer, Proceedings of Advancements in Medical Electronics.

Luo N, Dai W, Li C, et al. Flexible Piezoresistive Sensor Patch Enabling Ultralow Power Cuffless Blood Pressure Measurement, Advanced Functional Materials, 2016, 26(8):1178-1187.

* cited by examiner

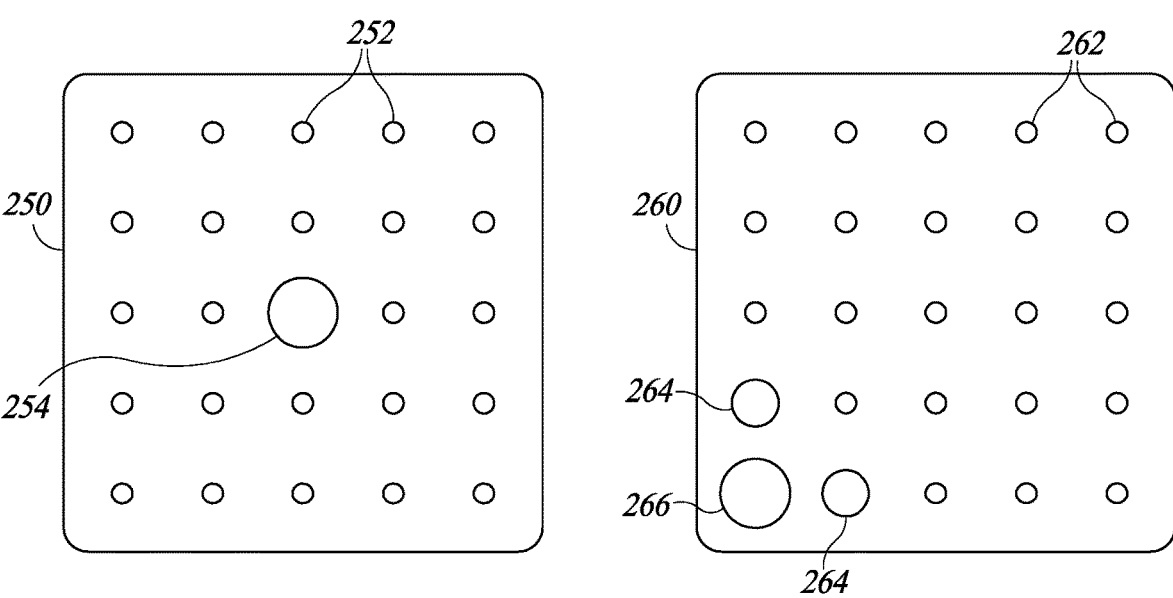
FIG. 14    FIG. 15
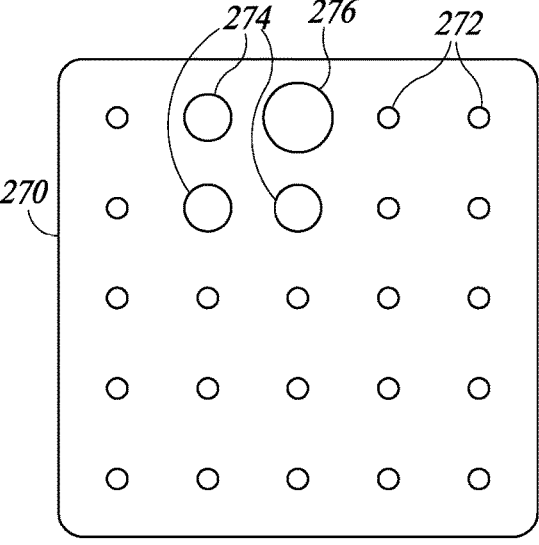
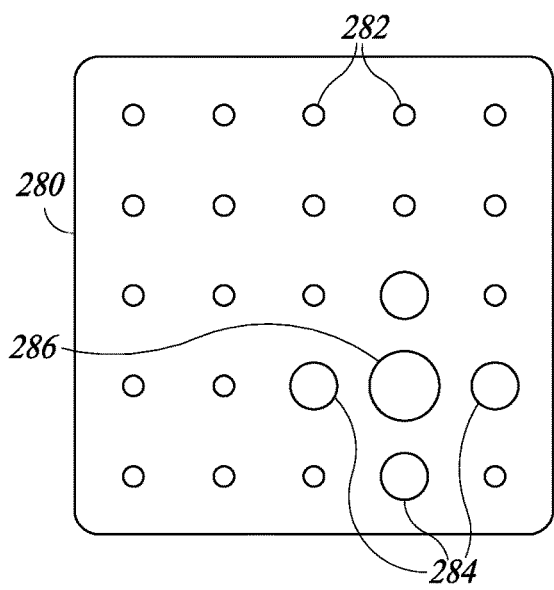
FIG. 16    FIG. 17

360
362

370
372

380
382

SYSTEM AND METHOD FOR PROVIDING USER FEEDBACK OF BLOOD PRESSURE SENSOR PLACEMENT AND CONTACT QUALITY

REFERENCE TO PRIORITY APPLICATION

This application claims the benefit of U.S. Provisional Application No. 62/442,917, filed Jan. 5, 2017, entitled "System and Method of Blood Pressure Sensor Contact Quality User Feedback," incorporated herein by reference in its entirety.

FIELD OF THE DISCLOSURE

The subject matter disclosed herein relates to the field of monitoring vital signs of a user and more particularly relates to a system and method for generating user feedback of the quality of the placement and contact of a blood pressure sensor on the user's body.

BACKGROUND OF THE INVENTION

High blood pressure is a common condition in which the long-term force of the blood against your artery walls is high enough that it may eventually cause health problems, such as heart disease. Blood pressure is determined both by the amount of blood your heart pumps and the amount of resistance to blood flow in your arteries. The more blood your heart pumps and the narrower your arteries, the higher your blood pressure.

One can have high blood pressure (i.e. hypertension) for years without any symptoms. Even without symptoms, damage to blood vessels and one's heart continues and can be detected. Uncontrolled high blood pressure increases one's risk of serious health problems, including heart attack and stroke. High blood pressure generally develops over many years, and it affects nearly everyone eventually. Fortunately, high blood pressure can be detected.

Currently, cardiovascular diseases represent a large proportion of all reported deaths globally. These diseases are considered a severe and shared risk, with a majority of the burden in low and middle-income countries. A major factor that increases the risk of heart failures or strokes, speeds up hardening of blood vessels and reduces life expectancy is hypertension or high blood pressure.

Hypertension is a chronic health condition in which the pressure exerted by the circulating blood upon the walls of blood vessels is elevated. In order to ensure appropriate circulation of blood in blood vessels, the heart of a hypertensive person must work harder than normal, which increases the risk of heart attack, stroke and cardiac failure. Eating a healthy diet and exercising, however, can significantly improve blood pressure control and decrease the risk of complications, Efficient drug treatments are also available. It is therefore important to find persons with elevated blood pressures and monitor their blood pressure information on a regular basis.

During each heartbeat, the blood pressure varies between a maximum (i.e. systolic) and a minimum (i.e. diastolic) pressure. A traditional noninvasive way to measure blood pressure has been to use a pressurized cuff and detect the pressure levels where the blood flow starts to pulsate (i.e. cuff pressure is between the systolic and diastolic pressure) and where there is no flow at all (i.e. cuff pressure exceeds systolic pressure). It has been seen, however, that users tend to consider the measurement situations, as well as the pressurized cuff tedious and even stressing, especially in long-term monitoring. In addition, the well-known white-coat syndrome tends to elevate the blood pressure during the measurement which leads to inaccurate diagnoses.

The use of wearable devices for monitoring body physiological parameters (e.g. blood pressure, heart rate (HR) pulse, body temperature, blood glucose level, movement patterns, etc.) non-invasively, continuously and/or intermittently for extended periods of time are becoming popular as a way to monitor and improve health.

Traditional blood pressure measurements require inflatable cuffs, which are gradually deflated from a state of full vessel occlusion to a lower pressure while listening using a mechanical sensor (e.g., stethoscope) to the sounds generated by the blood flow eddies in the vessel. An advantage of this method is its relative robustness to movements, while a disadvantage is its large form factor and the need for either manual inflation by the user or an automatic pump, which requires large quantities of energy. Since energy efficiency and small form factor are major requirements in wearable devices, inflatable cuff blood pressure sensing is not a useful paradigm in this space.

Prior art blood pressure measurement devices have significant disadvantages. First, the positioning or placement of the sensor on the radial artery is challenging to the user. Second, the sensor typically requires calibration in order to obtain correct readings. Third, the signal to noise ratio (SNR) obtained from the sensor might not be sufficient to obtain reliable blood pressure readings.

There is thus a need for a mechanism capable of continuously measuring and monitoring blood pressure that overcomes the disadvantages of traditional prior art devices and methods. For example, the mechanism of measuring blood pressure should not require the use of an inflatable cuff with its associated high energy requirements. In addition, the mechanism should be able to sense the blood pressure waveform on one or more of the arteries in the arm (i.e. the radial and ulnar arteries). Further, the mechanism preferably provides feedback related to the proper placement and contact of the blood pressure sensor on a user's body.

SUMMARY OF THE INVENTION

The present invention is a system and method for generating user feedback related to the quality of the placement and contact of a blood pressure sensor on a user's body. The sensor is incorporated in a wearable blood pressure measurement device that is capable of analyzing and providing feedback regarding the quality of placement and contact of the pressure sensor array. The wearable includes a pressure sensor array or a force resistive sensing sheet for blood pressure monitoring, means for attaching said pressure sensor to a user's body for measuring a region, a processing unit operative to record pressure signals from said sensor array and calculate quality of pressure sensor contact to measurement area score, and a display unit operative to determine and display the quality of the placement and contact of the pressure sensor. In one embodiment, a measurement score indicating the quality of the placement and contact of the pressure sensor is provided as feedback to the user.

The apparatus includes a pressure sensor array, or a force resistive sensing sheet for blood pressure monitoring, where in addition to the placement and contact quality score, directional indications are displayed to the user to either: (1) move the wearable device (e.g., wristband) left or right (clockwise or counterclockwise) along the organ (e.g., wrist) to position the center of the sensor array directly over the artery to be measured; (2) move the device (e.g., wristband) up or down along the organ (e.g., hand or other limb) to position the sensor array directly over the artery to be measured; and (3) tighten the device (e.g., wristband) to bring the sensor array closer and/or in contact with the artery to be measured.

It is appreciated that the wearable device apparatus can be used on any organ or limb of the body. For example, the device can be used on the arm, wrist, leg, etc. as long as pressure from an artery or blood vessel can be detected.

In another embodiment, the placement and contact quality user feedback of the wristband is translated into a number of ladders (e.g., via lit or flashing LEDs) on the wristband itself required to fasten the wristband securely enough in order to get a contact quality reading sufficient for measurement purposes.

There is thus provided in accordance with the invention, a method of providing feedback to a user relating to quality of placement and contact of a blood pressure sensor in a wearable device, the method comprising receiving data from the blood pressure sensor, calculating a quality metric in accordance with the sensor data, and providing feedback to the user in accordance with the quality metric.

There is also provided in accordance with the invention, an apparatus for providing feedback to a user relating to quality of placement and contact of a blood pressure sensor in a wearable device, comprising a wristband for attachment to a user's body, a pressure sensor array mounted on the wristband, the pressure sensor array including one or more pressure sensors, a processor coupled to a memory and operative to receive sensor data from the pressure sensor array and calculate therefrom a quality metric related to quality of placement and contact of the pressure sensor array on the user, generate user feedback based on the quality metric, and a feedback unit coupled to the processor, the feedback unit operative to convey the user feedback to the user.

There is further provided in accordance with the invention, a wearable device for measuring blood pressure of a user, comprising a wristband for attachment to a user's body, a housing mounted on the wristband, a display mounted in the housing for displaying blood pressure data, a pressure sensor array mounted on the wristband, the pressure sensor array including one or more pressure sensors and operative to acquire a blood pressure signal, a processor coupled to a memory, the processor operative to receive sensor data from the pressure sensor array and calculate therefrom a quality metric related to quality of placement and contact of the pressure sensor array on the user's person, generate user feedback based on the quality metric, if the quality metric exceeds a threshold, generate a blood pressure measurement for indicating on the display, and a feedback unit coupled to the processor, the feedback unit operative to convey the user feedback to the user.

BRIEF DESCRIPTION OF THE DRAWINGS

The present invention is explained in further detail in the following exemplary embodiments and with reference to the figures, where identical or similar elements may be partly indicated by the same or similar reference numerals, and the features of various exemplary embodiments being combinable. The invention is herein described, by way of example only, with reference to the accompanying drawings, wherein:

4

Figure 1:
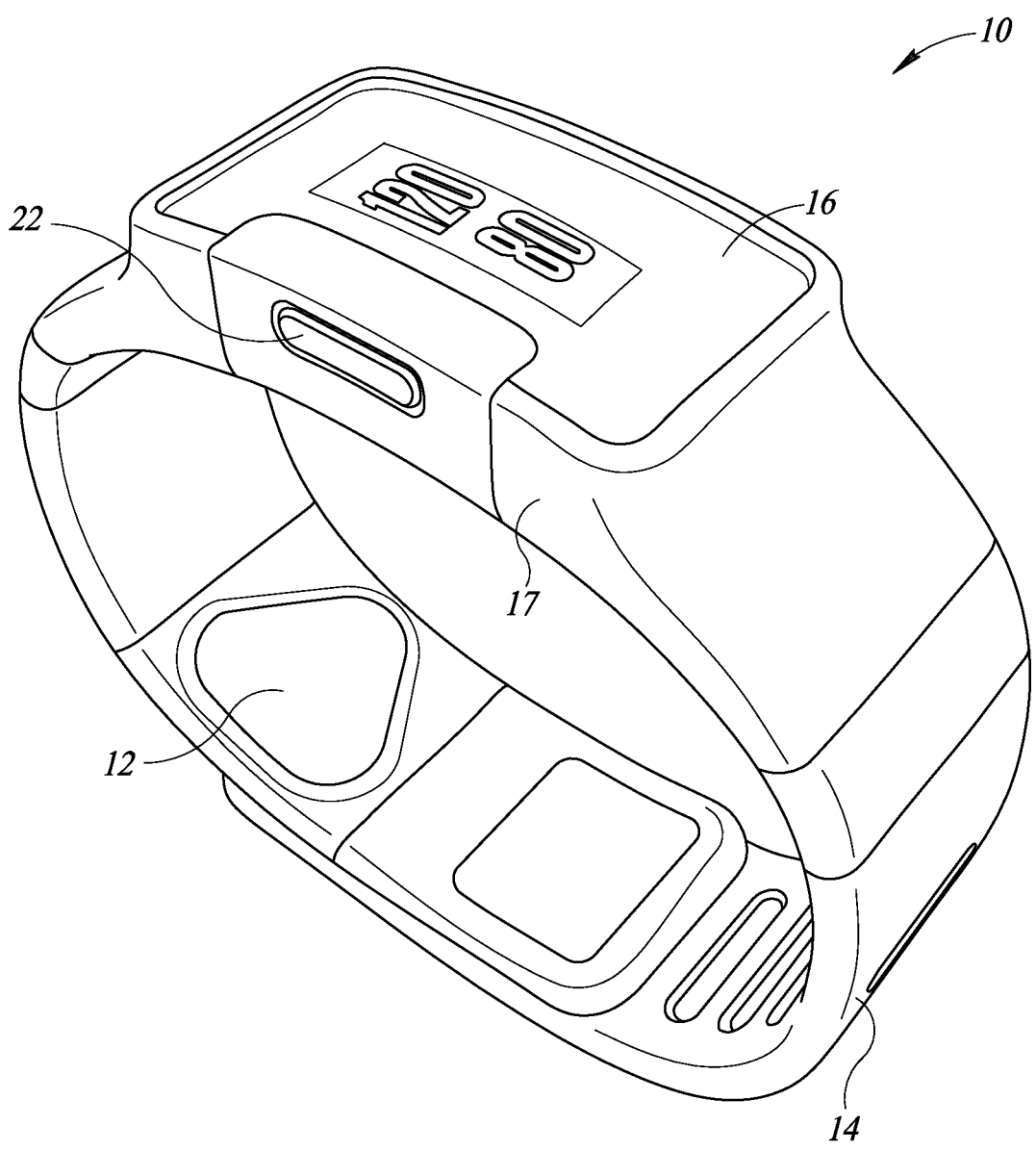
Figure 2:
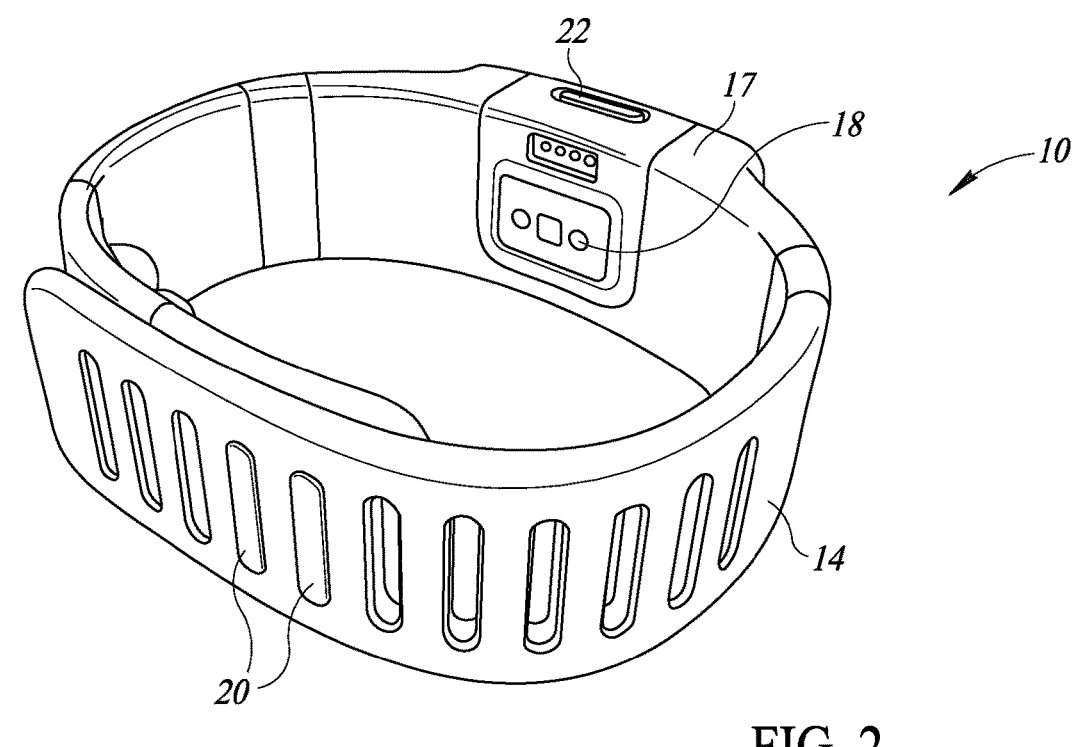
Figure 3:
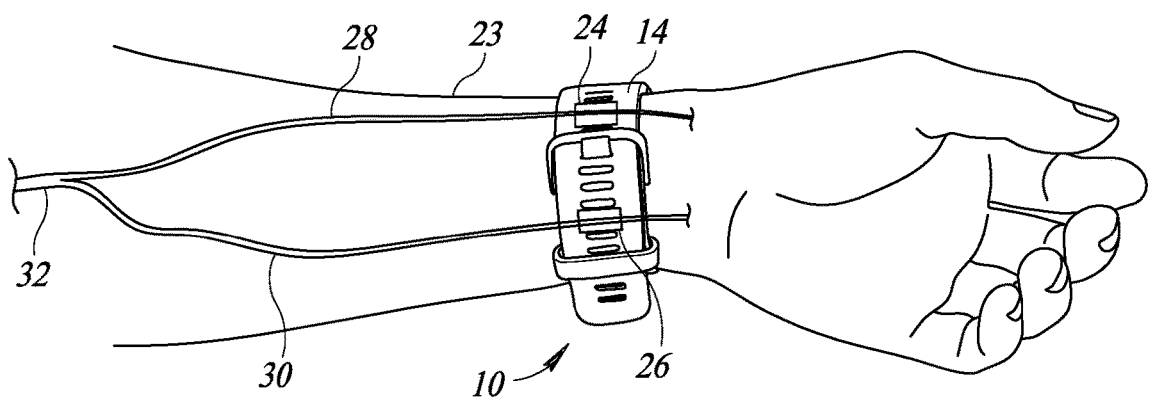
Figure 4:
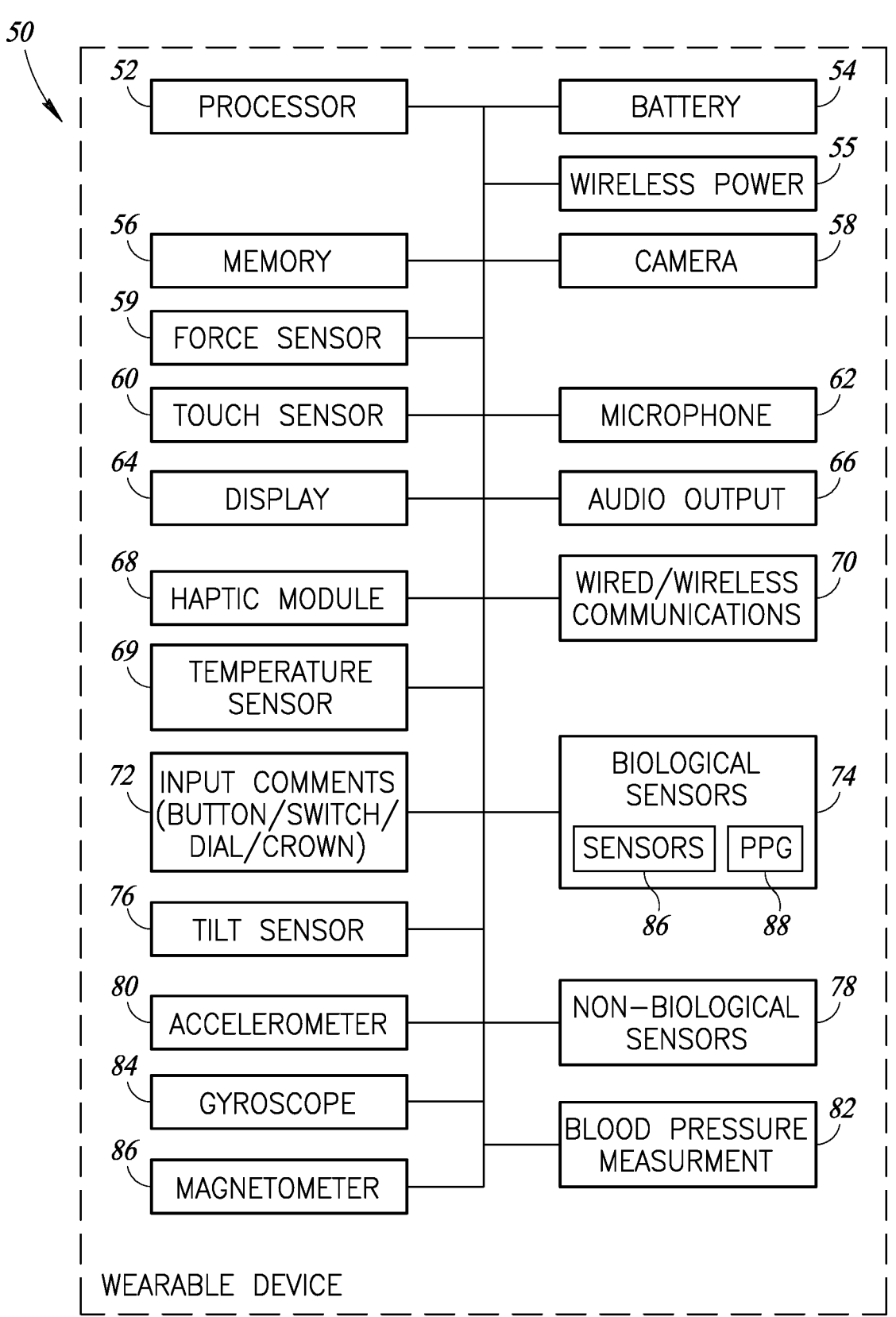
Figure 5:
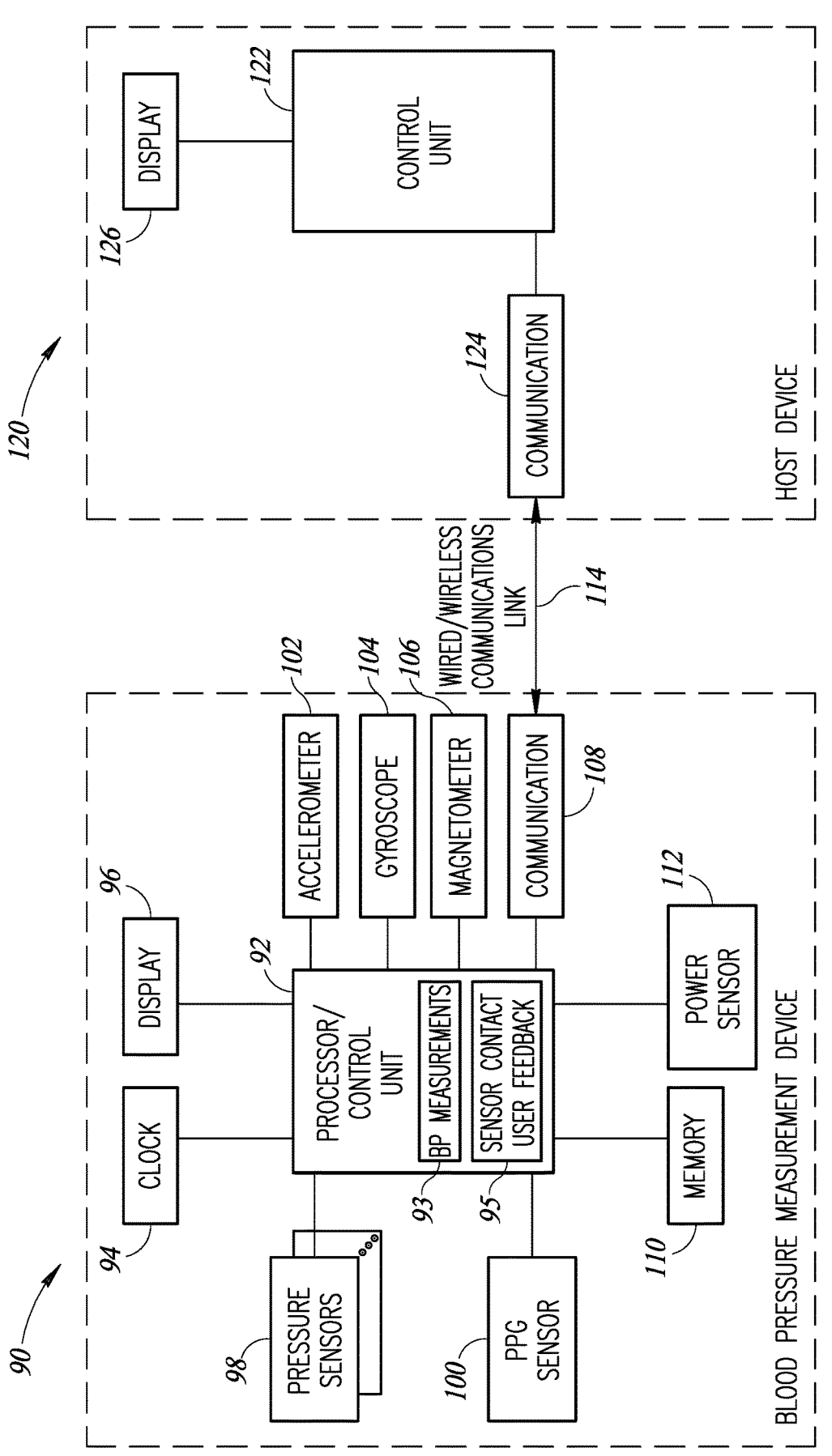
Figure 6:
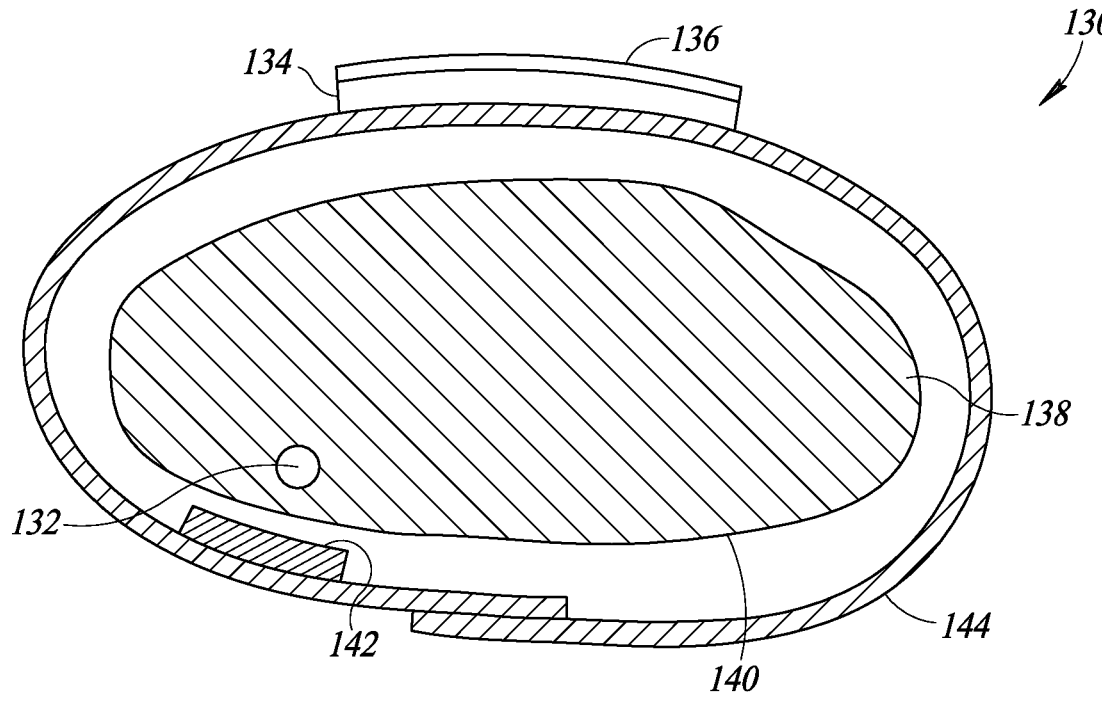
Figure 7:
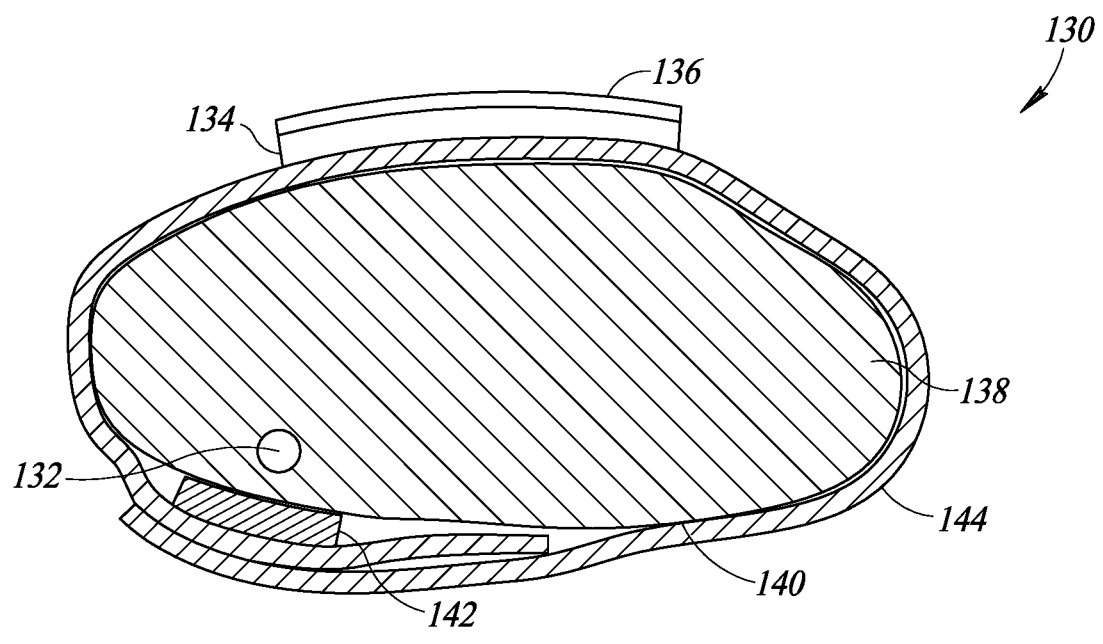
Figure 8:
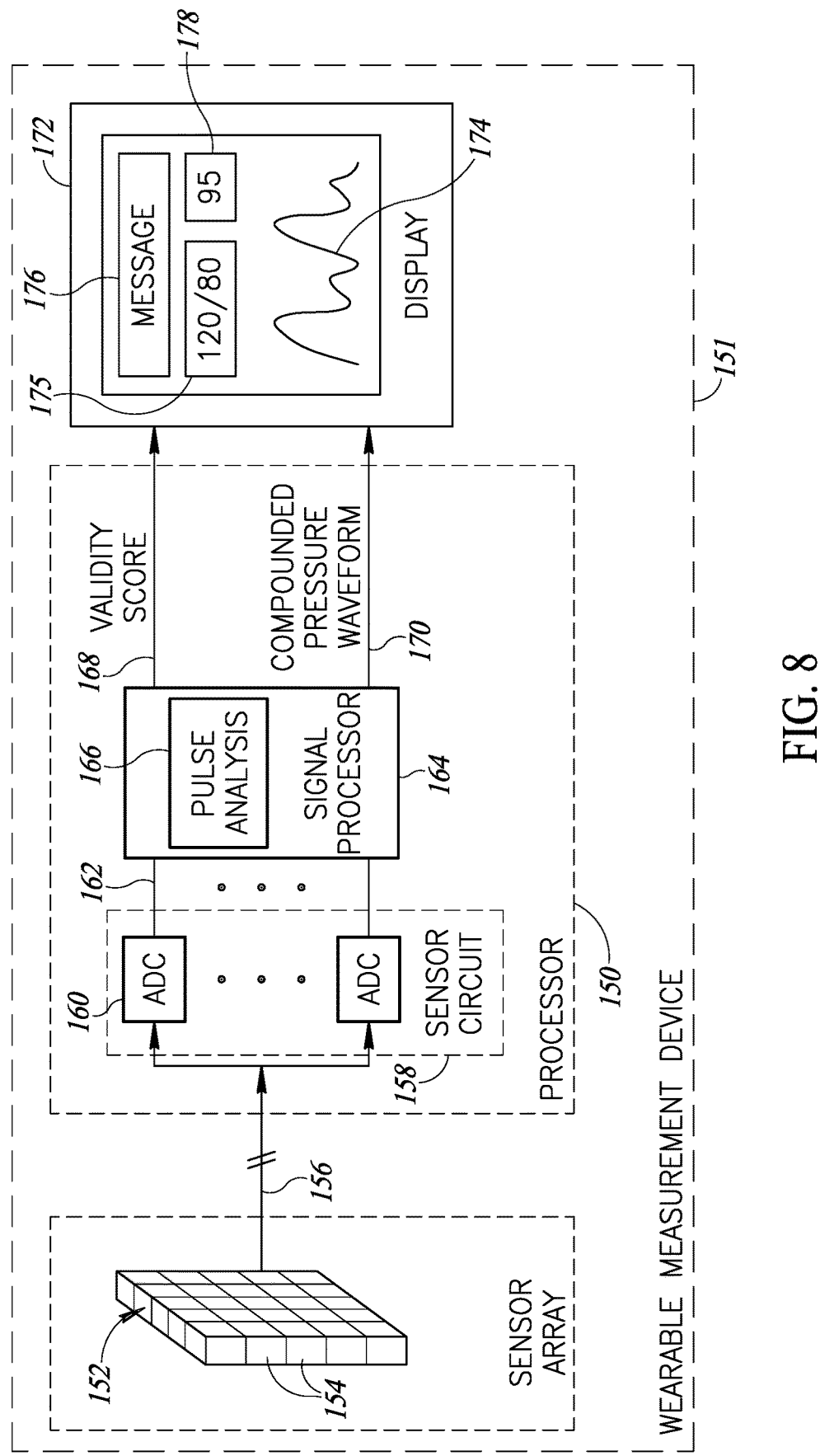
Figure 9:
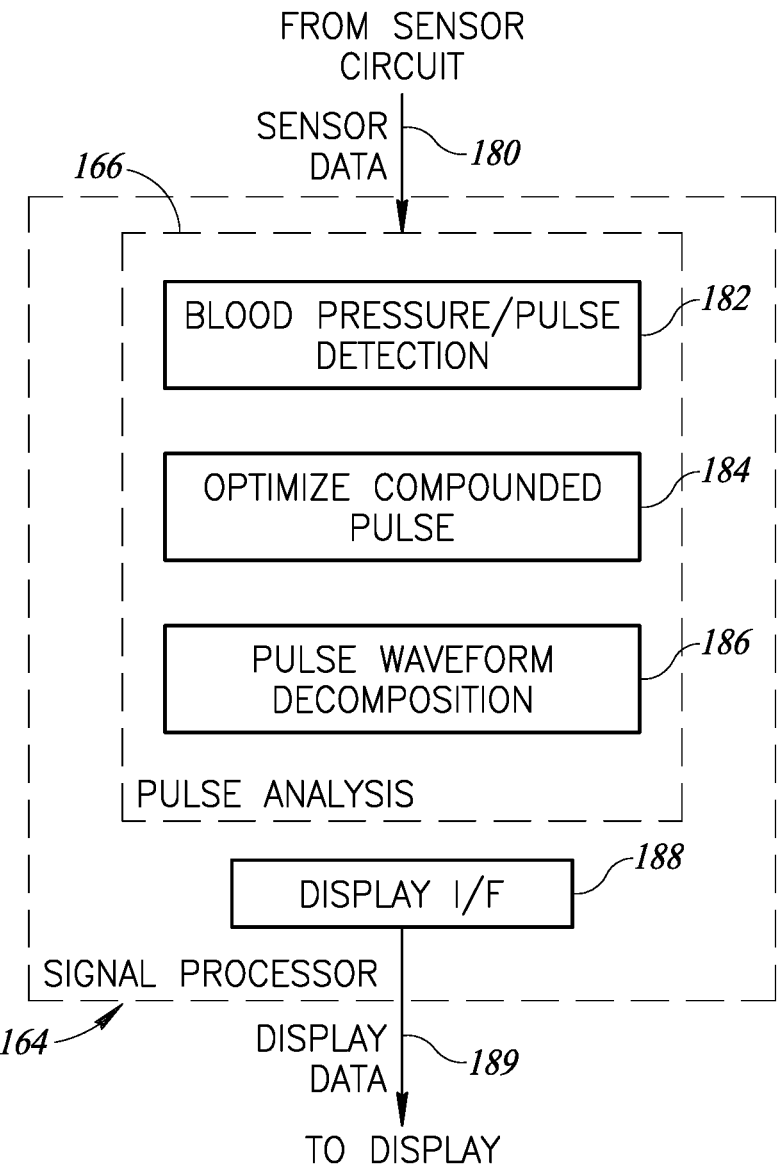
Figure 10:
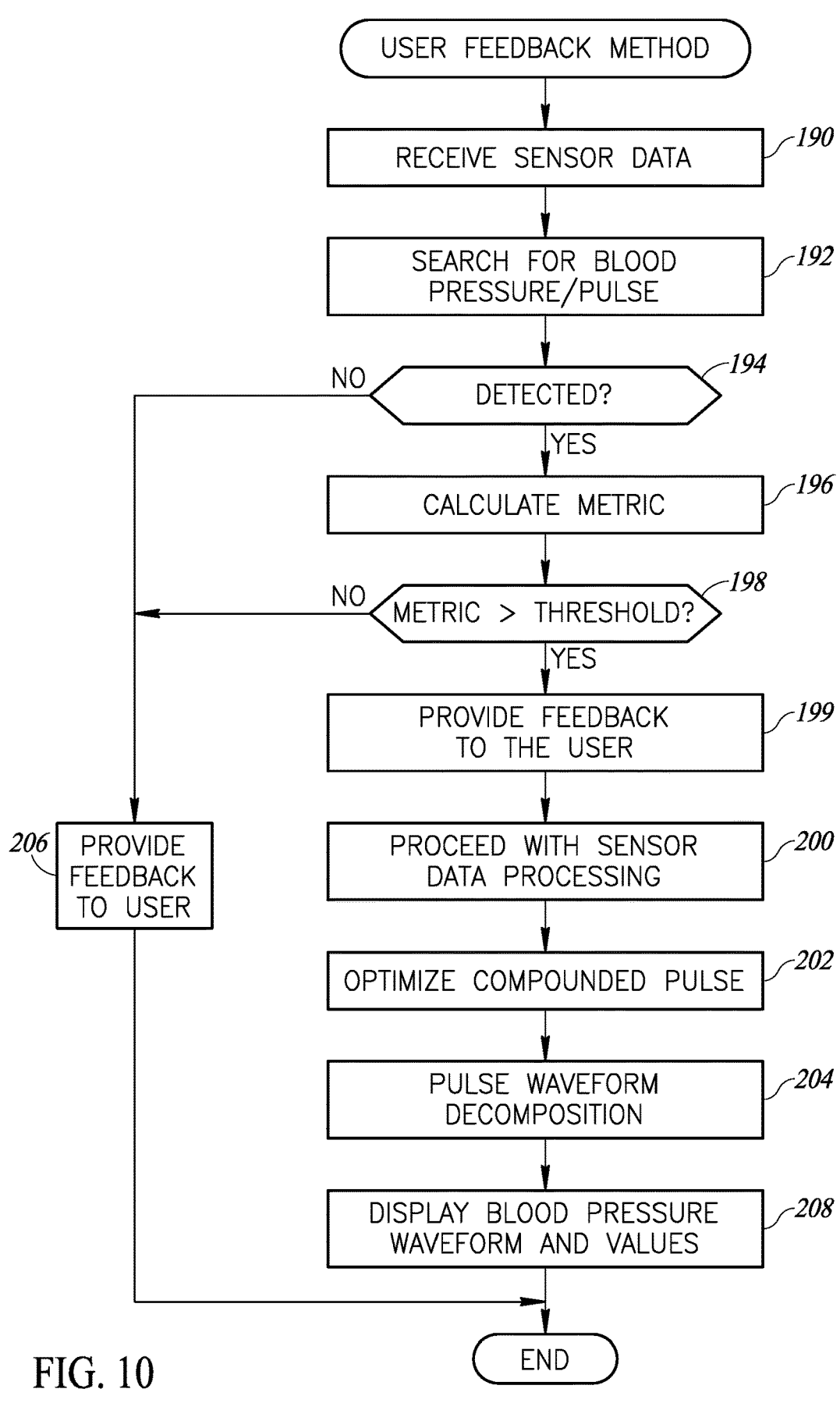
Figure 11:
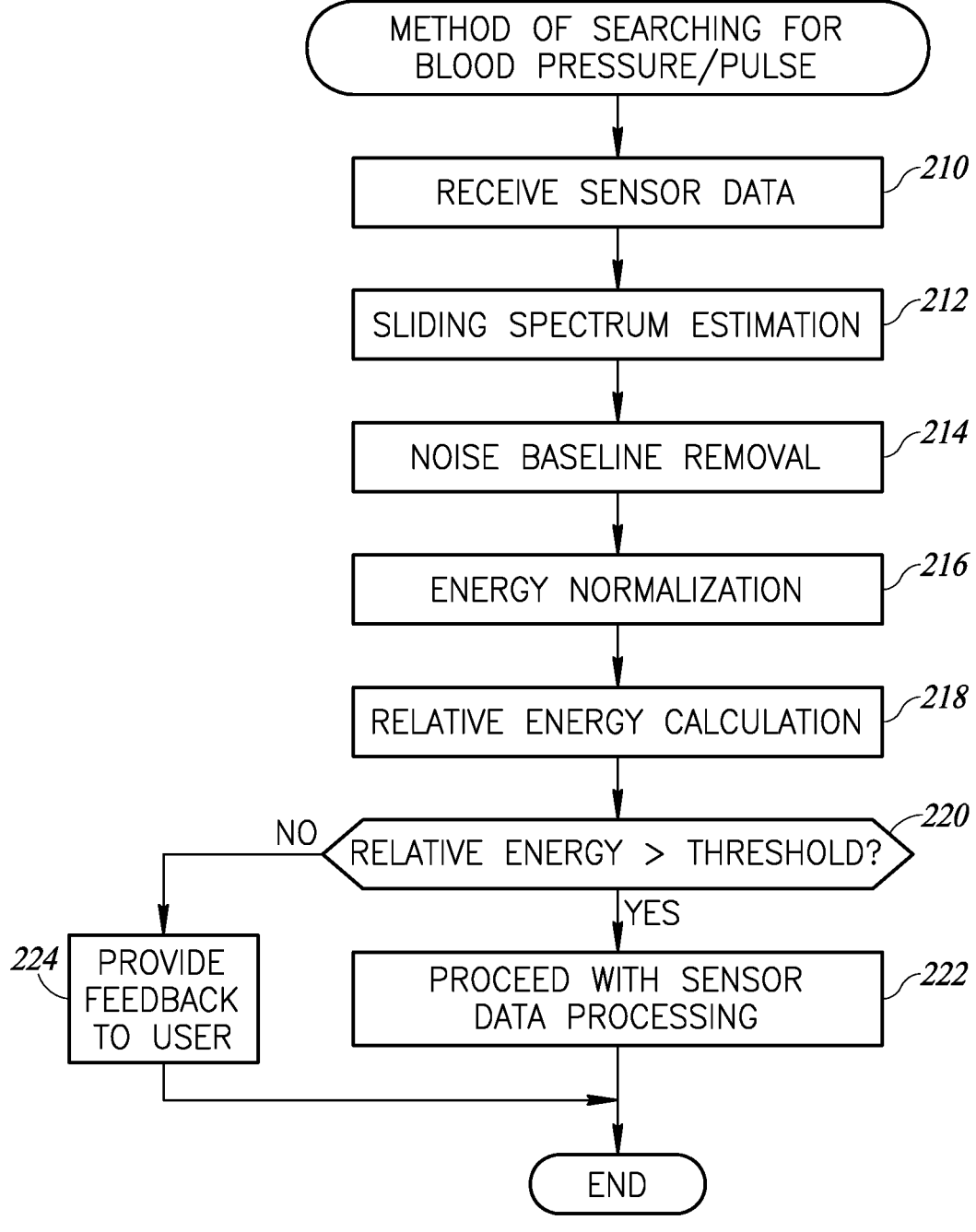
Figure 12:
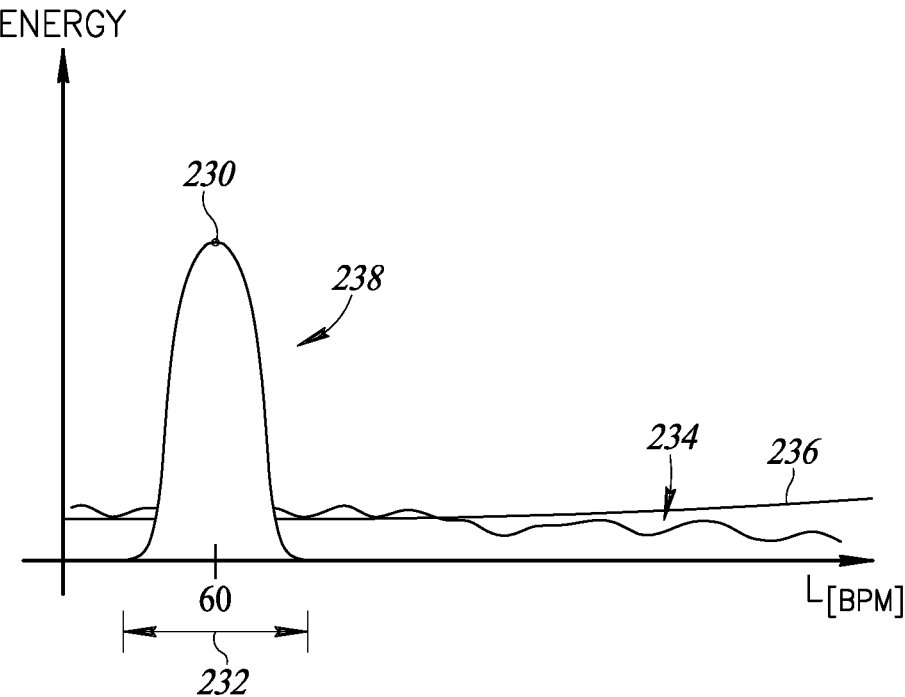
Figure 13:
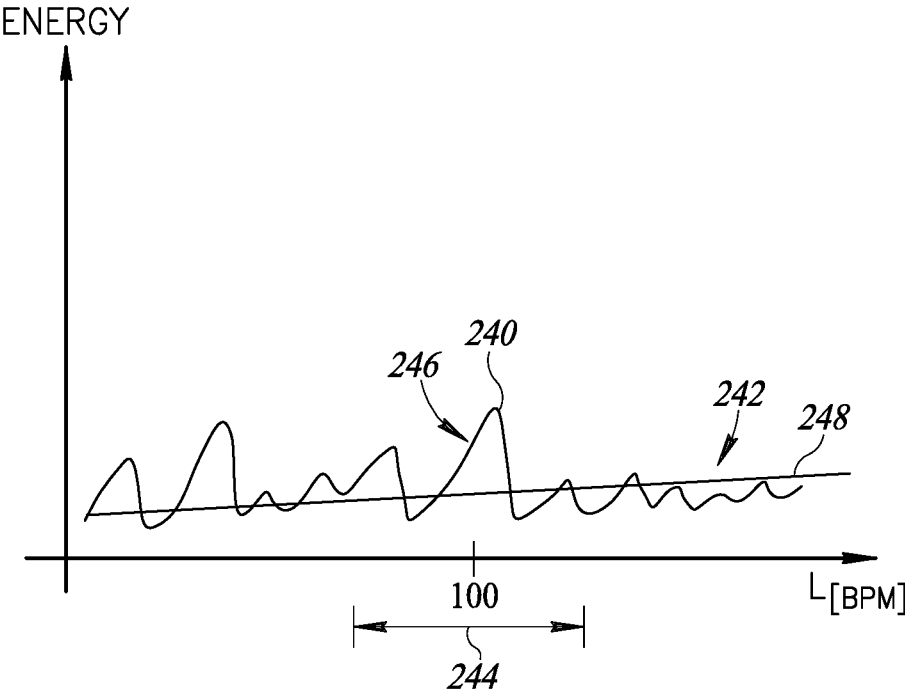
Figure 18:
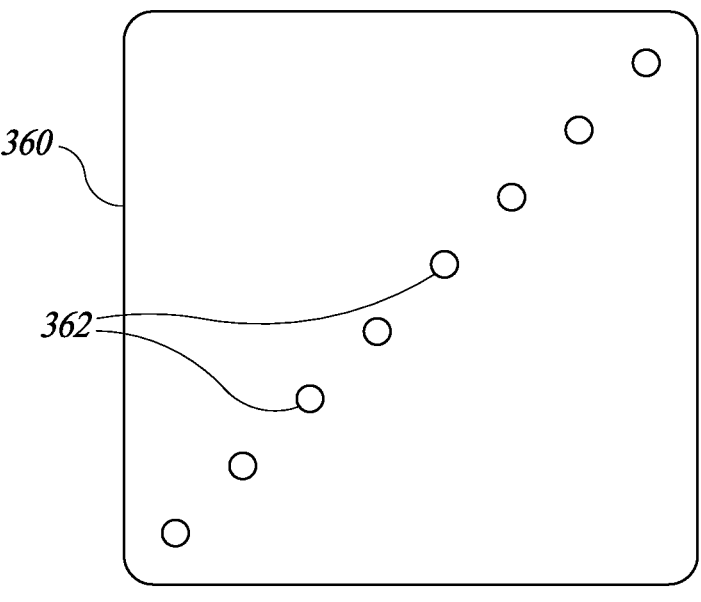
Figure 19:
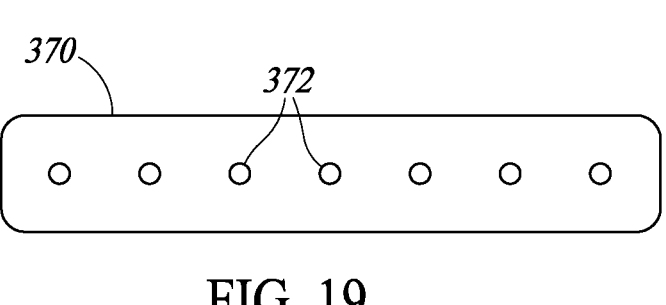
Figure 20:
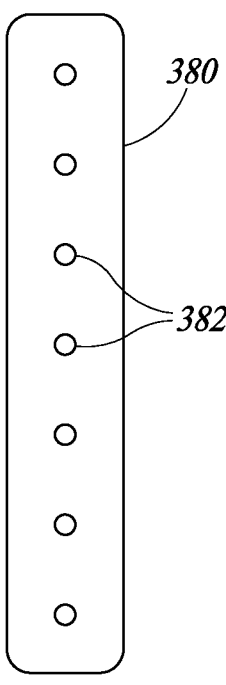
Figure 21:
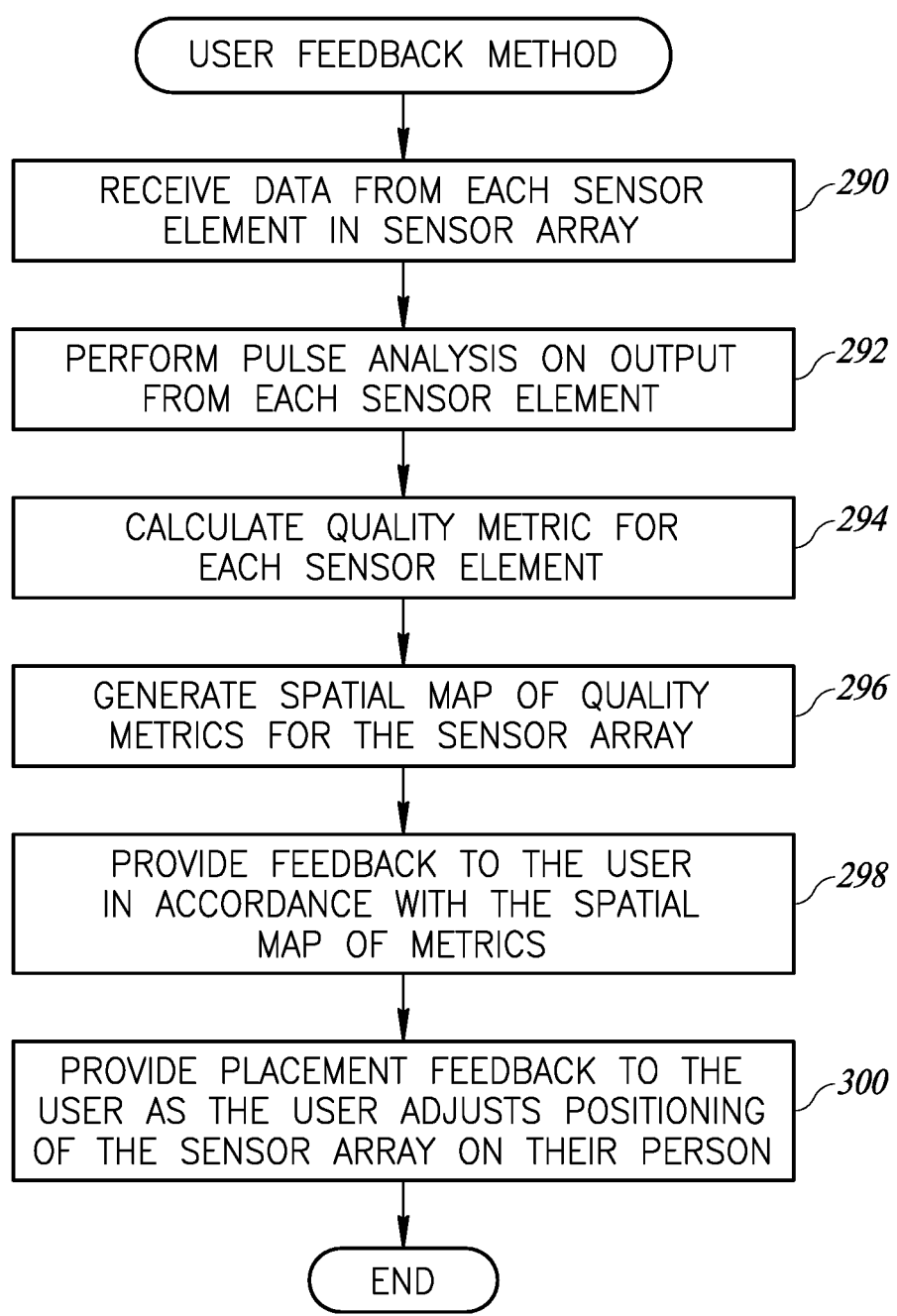
Figure 22:
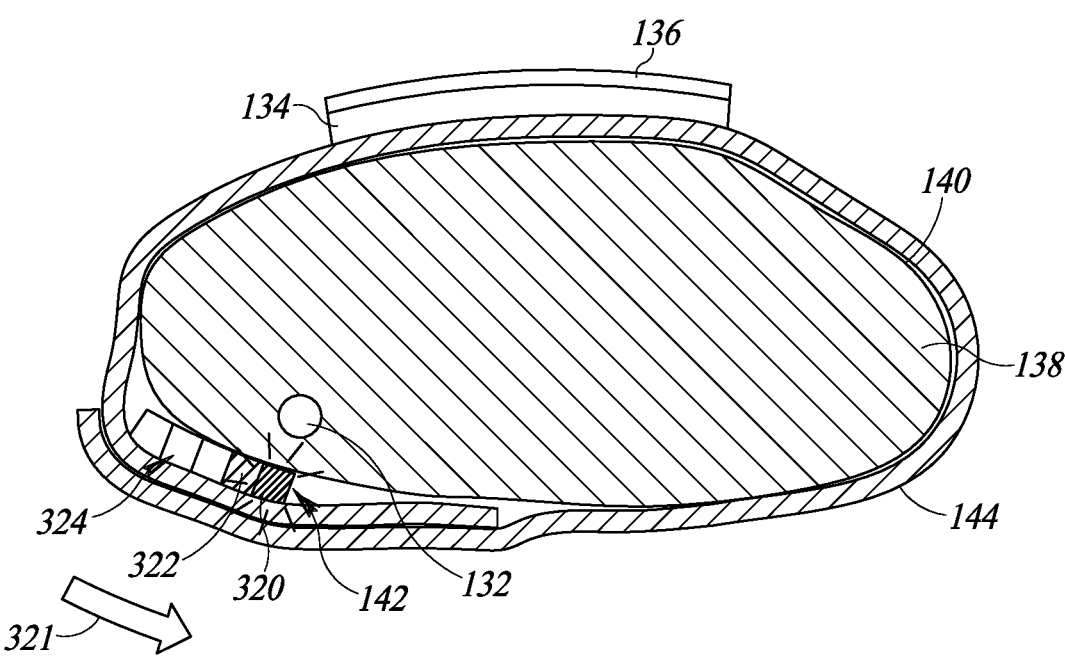
Figure 23:
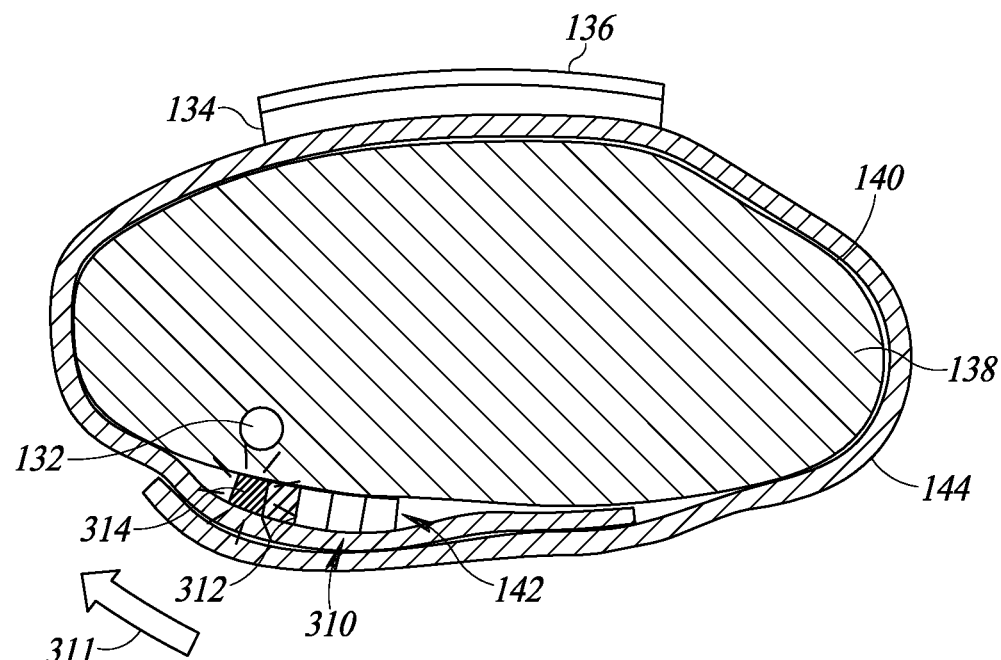
Figure 24:
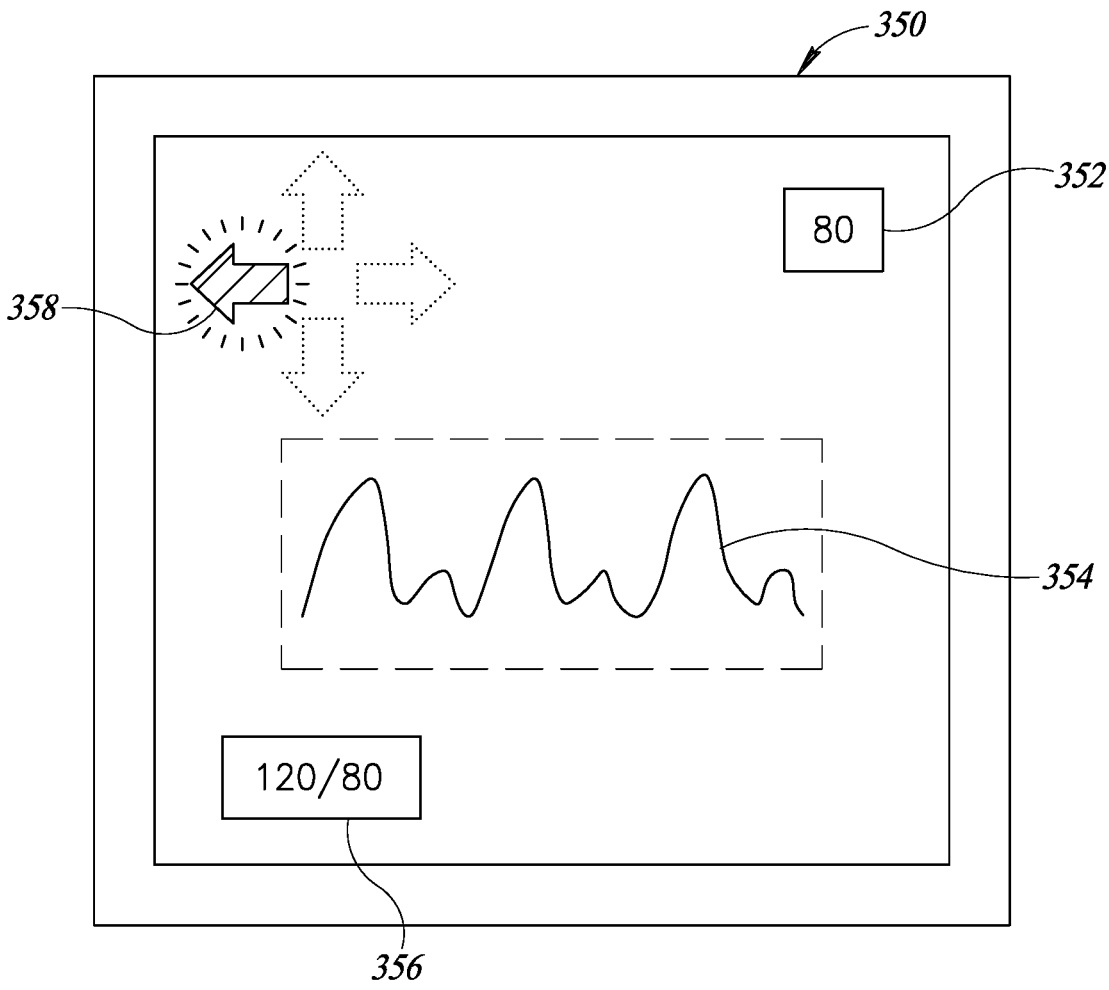

FIG. 1 is a diagram illustrating a first view of an example wearable device of the present invention operative to measure a user's blood pressure and provide sensor contact quality user feedback;

FIG. 2 is a diagram illustrating a second view of an example wearable device of the present invention operative to measure a user's blood pressure and provide sensor contact quality user feedback;

FIG. 3 is a diagram illustrating pressure sensors incorporated within a wearable device and configured to sense pressure from the radial and/or the ulnar artery;

FIG. 4 is a high-level block diagram illustrating an example wearable electronic device incorporating the sensor contact quality user feedback mechanism of the present invention;

FIG. 5 is a high-level block diagram illustrating an example blood pressure measurement device such as a wearable in communication with an optional host device;

FIG. 6 is a diagram illustrating a side view of a wrist band wearable in a loose state in accordance with an embodiment of the present invention;

FIG. 7 is a diagram illustrating a side view of a wrist band wearable in a snug state in accordance with an embodiment of the present invention;

FIG. 8 is a high level block diagram illustrating an example wearable measurement device in accordance with the present invention;

FIG. 9 is a high level block diagram illustrating an example signal processor portion of the wearable measurement device of the present invention;

FIG. 10 is a flow diagram illustrating an example user feedback method in accordance with the present invention;

FIG. 11 is a flow diagram illustrating an example method of searching for a blood pressure/pulse signal in accordance with the present invention;

FIG. 12 is a diagram illustrating an example sensor signal that does not exhibit blood pressure characteristics;

FIG. 13 is a diagram illustrating an example sensor signal that exhibits blood pressure characteristics;

FIG. 14 is a diagram illustrating a first example of sensor contact quality user feedback generated by the present invention;

FIG. 15 is a diagram illustrating a second example of sensor contact quality user feedback generated by the present invention;

FIG. 16 is a diagram illustrating a third example of sensor contact quality user feedback generated by the present invention;

FIG. 17 is a diagram illustrating a fourth example of sensor contact quality user feedback generated by the present invention;

FIG. 18 is a diagram illustrating a fifth example of sensor contact quality user feedback generated by the present invention;

FIG. 19 is a diagram illustrating a sixth example of sensor contact quality user feedback generated by the present invention;

FIG. 20 is a diagram illustrating a seventh example of sensor contact quality user feedback generated by the present invention;

FIG. 21 is a flow diagram illustrating an example user feedback method in accordance with the present invention;

FIG. 22 is a diagram illustrating an eighth example of sensor contact quality user feedback generated by the present invention;

FIG. 23 is a diagram illustrating a ninth example of sensor contact quality user feedback generated by the present invention; and FIG. 24 is a diagram illustrating a tenth example of sensor contact quality user feedback generated by the present invention.

DETAILED DESCRIPTION

In the following detailed description, numerous specific details are set forth in order to provide a thorough understanding of the invention. It will be understood by those skilled in the art, however, that the present invention may be practiced without these specific details. In other instances, well-known methods, procedures, and components have not been described in detail so as not to obscure the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary, for the understanding and appreciation of the underlying concepts of the present invention and in order not to obfuscate or distract from the teachings of the present invention.

Any reference in the specification to a method should be applied mutatis mutandis to a system capable of executing the method. Any reference in the specification to a system should be applied mutatis mutandis to a method that may be executed by the system.

Throughout the specification and claims, the following terms take the meanings explicitly associated herein, unless the context clearly dictates otherwise. The phrases "in one embodiment," "in an example embodiment," and "in some embodiments" as used herein do not necessarily refer to the same embodiment(s), though it may. Furthermore, the phrases "in another embodiment," "in an alternative embodiment," and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

A diagram illustrating a first view of an example wearable device of the present invention operative to measure a user's blood pressure from the radial and/or the ulnar artery is shown in FIG. 1. A diagram illustrating a second view of an example wearable device of the present invention operative to measure a user's blood pressure is shown in FIG. 2. A diagram illustrating pressure sensors incorporated within a wearable device and configured to sense pressure from the radial and/or the ulnar artery is shown in FIG. 3.

With reference to FIGS. 1, 2, and 3, the wearable device, generally referenced 10, comprises a display 16 (e.g., viewable OLED, etc.) mounted in a housing 17 containing a CPU, memory, wired and wireless communications, etc., one or more buttons, switches or dials 22, wristband (wrist strap(s)) 14 housing a pressure sensor array 12 that includes one or more pressure sensors 24, 26 adapted to sense pressure of the radial 28 and/or ulnar 30 arteries, one or more optical or other non-pressure sensors 18, and strap closure, clasp, holding, fastening or lock mechanism 20. The wrist band strap has an embedded pressure sensor on it and is intended to be closed against the wrist whilst applying sensor array 12 on at least one of the radial, ulnar and brachial arteries and apply medium pressure thereon (i.e. significantly less than the systolic pressure but enough to sense the pressure wave).

In one example, the wearable consumer product device 10 is a wearable multifunctional electronic device including multiple functionalities such as time keeping, health monitoring, sports monitoring, medical monitoring, communications to a host device and/or a cloud server, navigation, computing operations, and/or the like. The functionalities may include but are not limited to: keeping time; monitoring a user's physiological signals (e.g., heart rate, blood pressure, etc.) and providing health-related information based on those signals; communicating (in a wired or wireless fashion) with other electronic devices or services, which may be different types of devices having different functionalities; providing alerts to a user, which may include audio, haptic, visual and/or other sensory output, any or all of which may be synchronized with one another; visually depicting data on a display; gathering data form one or more sensors that may be used to initiate, control, or modify operations of the device; determining a location of a touch on a surface of the device and/or an amount of force exerted on the device, and using either or both as input; accepting voice input to control one or more functions; accepting tactile input to control one or more functions; capturing and transmitting images; and so on.

The device 10 can take a variety of forms. In one example, the device is a wrist worn electronic device. The device may include a variety of types of form factors including, wristbands, armbands, bracelets, jewelry, and/or the like.

A wearable consumer product is one that can be worn by or otherwise secured to a user. Note that a wearable consumer product can be worn by a user in a variety of ways such as around the wrist. In this case, the device includes a wristband or wrist strap that can be wrapped around a user's wrist to secure the device to the user's body. The device may include one or more other types of attachments including, for example, an armband, lanyard, waistband, chest strap, etc.

In one embodiment, the device comprises a housing 17 that carries, encloses and supports both externally and internally various components (including, for example. integrated circuit chips and other circuitry) to provide computing and functional operations for the device. The components may be disposed on the outside of the housing, partially within the housing, through the housing, completely inside the housing, and the like. The housing may, for example, include a cavity for retaining components internally, holes or windows for providing access to internal components, and various features for attaching other components. The housing may also be configured to form a water resistant or waterproof enclosure. For example, the housing may be formed from as a single unitary body and the openings in the unitary body may be configured to cooperate with other components to form a water-resistant or waterproof barrier. In another embodiment, the housing may not comprise a cavity but rather is constructed from plastic where the device electronics are molded into the plastic.

Examples of components that may be contained in the device include processing units, signal processors, memory, display, sensors, biosensors, speakers, microphones, haptic actuators, accelerometers, gyroscopes, batteries, and so on. In some cases, the device may take on a small form factor. In cases such as these, the components may be packaged and/or in order to provide the most functionality in the smallest space. The components may also be configured to take up a minimal amount of space, which may facilitate the device having a small form factor. Additionally, the integration and assembly of the various components may be configured to enhance the reliability of the device.

The construction of the housing may be widely varied. For example, housing may be formed from a variety of materials including plastic, rubber, wood, silicone, glass, ceramics, fiber composites, metal or metal alloys, (e.g., stainless steel, aluminum), precious metals (e.g., gold, silver), or other suitable materials, or a combination of these materials.

Also in the illustrated embodiment, the wearable electronic device includes a band 14 or strap or other means for attaching to a user's arm 23. The band may, for example, be configured to attach to the body and provide a loop for securing to the wrist of the user. The band may be integral with the housing or it may be a separate part. If integral, the band can be a continuation of the housing. In some cases, the integral band may be formed from the same material as the housing. If the band is separate, the band may be fixed or releasably coupled to the housing. In both cases, the band may be formed from similar or different materials as the housing. In most cases, the band is formed from a flexible material such as an elastomer such that it can conform to a user's body. Furthermore, the band itself may be a single integral part or it may include attachment ends that provide an open and closed configuration. The attachment ends may, for example, be manifested as a clasp or other similar attachment mechanism or device. This particular configuration allows a user to open the band for placement on the arm and close the band in order to secure the band and body to the arm. The band may be widely varied. By way of example, they may be formed from rubber, silicone, leather, metal, mesh, links and/or the like.

A high-level block diagram illustrating an example wearable electronic device incorporating the blood pressure measurement mechanism of the present invention is shown in FIG. 4. By way of example, device 50 may correspond to the consumer product 10 shown in FIGS. 1, 2, and 3 described supra. To the extent that multiple functionalities, operations, and structures are disclosed as being part of, incorporated into, or performed by device 50, it should be understood that various embodiments may omit any or all such described functionalities, operations, and structures. Thus, different embodiments of the device 50 may have some, none, or all of the various capabilities, apparatuses, physical features, modes, and operating parameters discussed herein.

The device 50 comprises one or more processing units 52 that are configured to access a memory 56 having instructions stored thereon. The instructions or computer programs may be configured to perform one or more of the operations or functions described with respect to the device 50. For example, the instructions may be configured to control or coordinate the operation of a display 64, one or more input/output components such as the touch sensor 60, etc., one or more communication channels 70, one or more sensors such as biological sensors 74 and non-biological sensors 78, a speaker 66, a microphone 62, and/or one or more haptic feedback devices 68.

The processing units 52 may be implemented as any electronic device capable of processing, receiving, or transmitting data or instructions. For example, the processing units may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

For example, the processor may comprise one or more general purpose CPU cores and optionally one or more special purpose cores (e.g., DSP core, floating point, etc.). The one or more general purpose cores execute general purpose opcodes while the special purpose cores execute functions specific to their purpose.

The memory 56 comprises dynamic random access memory (DRAM) or extended data out (EDO) memory, or other types of memory such as ROM, static RAM, flash, and non-volatile static random access memory (NVSRAM), removable memory, bubble memory, etc., or combinations of any of the above. The memory stores electronic data that can be used by the device. For example, a memory can store electrical data or content such as, for example, audio and video files, documents and applications, device settings and user preferences, timing and control signals or data for the various modules, data structures or databases, and so on. The memory can be configured as any type of memory.

The display 64 functions to present visual or graphical output to a user. In some embodiments, the display includes a graphical user interface produced using an operating system or software application executed on one or more processing units of the device. In one example, the display includes a graphical depiction that resembles a watch face or other timekeeping device. In other examples, the display includes a graphical interface for an e-mail, text messaging, or other communication-oriented program. The display may also present visual information that corresponds to one of the other functional aspects of the device 50. For example, the display may include information that corresponds to the input of the biosensor 74, non-biosensor 78, force sensor 59, touch sensor 60, and others.

Input components 72 may include buttons, switches, dials, and crowns for accepting user input, and so on. Generally, the input components are configured to translate a user provided input into a signal or instructions that may be accessed using instructions executed on the processor. In the present example, the input components may include the hardware configured to receive the user input (e.g., button, switch, crown, and encoder) which is operatively coupled to circuitry and firmware used to generate signals or data that are able to be accessed using processor instructions. Each input component may include specialized circuitry for generating signals or data and, additionally or alternatively, circuitry and firmware for generating signals or data may be shared between multiple input components. In some cases, the input components produce user provided feedback for application specific input that corresponds to a prompt or user interface object presented on display 64. For example, a crown may be used to receive rotational input from the user, which may be translated into an instruction to scroll a list or object presented on the display. The input components may also produce user input for system level operations. For example, the input components may be configured to interact directly with hardware or firmware being executed on the device for system level operations, including, without limitation, power on, power off, sleep, awake, and do-not-disturb operations.

The device 50 may also comprise one or more acoustic elements, including audio outputs 66 (e.g., speaker, headphone jack, etc.) and a microphone 62. The audio output 66 may include drive electronics or circuitry and may be configured to produce an audible sound or acoustic signal in response to a command or input. Similarly, the microphone may also include drive electronics or circuitry and is configured to receive an audible sound or acoustic signal in response to a command or input. The speaker and the microphone may be acoustically coupled to respective ports or openings in the housing that allow acoustic energy to pass, but may prevent the ingress of liquid and other debris.

The speaker and microphone are also operatively coupled to the processor, which may control the operation of the speaker and microphone. In some cases, the processor is configured to operate the speaker to produce an acoustic output that corresponds to an application or system-level operation being performed on the device 50. In some cases, the speaker is operatively coupled to other modules, including, for example, input components 72, such as a crown or button. In some implementations, the device is configured to produce an audible output that corresponds to the operation of the crown or buttons using the speaker. The microphone may be configured to produce an output or signal in response to an acoustic stimulus. For example, the microphone may be operatively coupled to the memory 56 and may be configured to record audio input, including human speech, music, or other sounds. In some cases, the microphone may be configured to receive voice signals, which may be interpreted as voice commands by the processor.

The one or more communication channels 70 may include one or more wired and/or wireless interface(s) that are adapted to provide communication between the processor 52 and an external device such as a host device 120 (FIG. 5). In general, the one or more communication channels may be configured to transmit and receive data and/or signals that may be interpreted by instructions executed on the processor. In some cases, the external device is part of an external communication network that is configured to exchange data with wireless devices. Generally, the wireless interface may include, without limitation, radio frequency, optical, acoustic, and/or magnetic signals and may be configured to operate over a wireless interface or protocol. Example wireless interfaces include radio frequency cellular interfaces, fiber optic interfaces, acoustic interfaces, Bluetooth interfaces (e.g., Bluetooth, Bluetooth Low Energy, etc.), infrared interfaces, USB interfaces, Wi-Fi interfaces, TCP/IP interfaces, network communications interfaces, or any conventional communication interfaces.

In some implementations, the one or more communications channels may include a dedicated wireless communication channel between the device and another user device, such as a mobile phone, tablet, computer, host device, or the like. In some cases, output, including audio sounds or visual display elements, are transmitted directly to the other user device for output to the user. For example, an audible alert or visual warning may be transmitted to a user's mobile phone for output on that device. Similarly, the one or more communications channels may be configured to receive user input provided on another user device. In one example, the user may control one or more operations on the device using a user interface on an external mobile phone, table, computer, or the like.

Additionally, the communications channels 70 may include a near field communication (NFC) interface. The NFC interface may be used to identify the device and initiate a secure data connection, which may be used to authorize transactions, purchases, or conduct other forms of e-commerce.

The device 50 also comprises one or more biological 74 and non-biological 78 sensors. Non-biological sensors 78 may include one or more different sensors, including devices and components that are configured to detect environmental conditions and/or other aspects of the operating environment. Examples include an ambient light sensor (ALS), proximity sensor, temperature sensor, barometric pressure sensor, moisture sensor, and the like. Thus, the non-biological 78 sensors may also be used to compute an ambient temperature, air pressure, and/or water ingress into the device. In some embodiments, non-biological 78 sensors may include one or more motion sensors for detecting movement and acceleration of the device. The one or more motion sensors may include one or more of the following: a tile sensor 76, accelerometer 80, gyroscope 84, magnetometer 86 or other type of inertial measurement device.

Motion sensor data can be used to monitor and detect changes in motion of the device. Changes in linear and angular motion may be used to determine or estimate an orientation of the device relative to a known location or fixed datum. The sensor input produced from the one or more motion sensors may also be used to track the movement of the user. The movement of the user may be used to facilitate navigation or map-guided functionality of the device. Additionally, input related to the gross movement of the user can be used as a pedometer or activity meter, which may be stored and tracked over time to determine health metrics or other health related information. Additionally, in some embodiments, sensor input from the one or more motion sensors may be used to identify motion gestures. For example, the motion sensors can be used to detect an arm raise or the position of a user's body (within a predetermined confidence level of certainty).

The device 50 also comprises one or more biological sensors (biosensors) 74 that may include optical and/or electronic biometric sensors that may be used to compute one or more health metrics. One or more of the biosensors may include one or more pressure sensors 86 for measuring blood pressure, a light source and a photodetector to form a photoplethysmography (PPG) sensor 88. The optical (e.g., PPG) sensor or sensors may be used to compute various health metrics including, without limitation, heart rate, a respiration rate, blood oxygenation level, blood volume estimate, blood pressure, or a combination thereof. One or more of the biosensors may also be configured to perform an electrical measurement using one or more electrodes in contact with the user's body. The electrical sensor(s) may be used to measure electrocardiographic (ECG) characteristics, galvanic skin resistance, and other electrical properties of the user's body. Additionally, or alternatively, one or more of the biosensors may be configured to measure body temperature, exposure to UV radiation, and other health related information. The device map also comprises one or more temperature sensors 69 for measuring the body temperature of a user.

The device 50 may also comprise one or more haptic devices 68. The haptic device may include one or more of a variety of haptic technologies such as, but not necessarily limited to, rotational haptic devices, linear actuators, piezoelectric devices, vibration elements, and so on. In general, the haptic device may be configured to provide punctuated and distinct feedback to a user of the device. More particularly, the haptic device may be adapted to produce a knock or tap sensation and/or a vibration sensation. The haptic device may be operatively coupled to the processor 52 and memory 56. In some embodiments, the haptic device may be directly controlled by the processor. In some embodiments, the haptic device may be controlled, at least in part, by the operation of an input component 72, including, for example, a button, dial, crown, or the like. The operation of the haptic device may also be paired or linked to the operation of one or more other output devices, including, for example, the display 64 or audio output device 66, e.g., a speaker. In one embodiment, haptic output may be produced using one or more electromechanical subassemblies that are configured to induce motion or vibration in the device, which may be perceived or sensed by the user.

The device 50 may comprise a battery or other suitable power source 54 that is used to store and provide power to the other components of the device. The battery may be a rechargeable power supply that is configured to provide power to the device while it is being worn by the user. The device may also be configured to recharge the battery using a wireless charging system. Accordingly, in some cases, the device may include a wireless power module 55 that may be configured to receive power from an external device or dock. The wireless power module may be configured to deliver power to components of the device, including the battery.

In some implementations, the device includes one or more receiving inductive coils that are configured to cooperate with one or more transmitting inductive coils that are located in a charging dock or other external device. The wireless charging system allows the transfer of power and/or wireless communications with the device without the use of an external port or terminal connection.

The wireless power module and an external charging station or dock may also be configured to transmit data between the device and a base or host device. In some cases, the wireless power module may interface with the wireless charging station or dock to provide an authentication routine that is able to identify specific hardware, firmware, or software on the device in order to facilitate device maintenance or product updates.

The device 50 may also comprise a variety of other components, including for example, a camera or camera modules 58. The camera may be configured to capture an image of a scene or subject located within a field of view of the camera. The image may be stored in a digital file in accordance with any one of a number of digital formats. In some embodiments, the device includes a camera, which includes an image sensor formed from a charge-coupled device (CCD) and/or a complementary metal-oxide-semiconductor (CMOS) device. The camera may also include one or more optical components disposed relative to the image sensor, including, for example, a lens, a filter, a shutter, and so on.

The device 50 may comprise a force sensor 59 configured to detect and measure the magnitude of a force of a touch on a surface of the device. The output of the force sensor can be used to control various aspects of the device. For example, the force sensor may be used to control an aspect, such as a cursor or item selection on a user interface presented on the display of the device. The force sensor may also be used to control the audio output, haptic output, and other functionality of the device. The force sensor may also be used to distinguish between different types of input from the user. For example, a light touch from the user may be interpreted as a scroll command and used to index or scroll through a list of items on the display. A harder touch from the user may be interpreted as a selection or confirmation of an item on the display.

The device 50 also may comprise a touch sensor 60 configured to detect and measure the location of a touch on a surface of the device. In some implementations, the touch sensor is a capacitive based touch sensor that is disposed relative to the display or display stack of the device. The touch sensor may be a separate nonintegrated sensor relative to the force sensor. In alternative embodiments, the touch sensor may also be physically and/or logically integrated with the force sensor to produce a combined output. The touch sensor may be used to control various aspects of the device, e.g., to control an aspect of the user interface presented on the display of the device, the audio output, haptic output, and other functionality of the device.

In some cases, the logical integration of the force sensor 59 and touch sensor 60 enhances the versatility or adaptability of device 50 by enabling a sophisticated user interface. For example, they may be combined to interpret a wider range of gestures and input commands than may be possible using, for example, only a touch input. For example, the force sensor may provide a magnitude of a force of a touch, which may be used to distinguish between two touch input commands that have a similar location or gesture path. An improved touch interface using both force sensor and touch sensor may be particularly advantageous when interpreting touch commands on a relatively small area surface, such as a display screen or cover glass of a wearable electronic device.

A high-level block diagram illustrating an example blood pressure measurement device such as a wearable in communication with an optional host device is shown in FIG. 5. The blood pressure measurement device, generally referenced 90, comprises a control unit/processor 92 incorporating, inter alia, blood pressure measurement processing block 93, sensor placement and contact user feedback block 95, clock source 94 such as a crystal oscillator, display 96, communications module 108, memory 110, power source 112, one or more pressure sensors 98, PPG sensor 100, and one or more motions sensors such as 3D Microelectrome- chanical system (MEMS) accelerometer 102, gyroscope 104 and/or magnetometer 106. The host device, generally refer- enced 120, comprises a control unit or processor 122, display 126 and communications module 124. Note that the device 90 may be incorporated into a wearable device such as shown in FIG. 4 described in detail supra.

Note that the one or more pressure sensors may comprise (1) a microelectromechanical system (MEMS) capacitive pressure sensor; (2) a patch sensor applied to the brachial artery; (3) an array of pressure sensors simultaneously collecting pressure data; (4) a pressure sensor array opera- tive to generate a single pressure measurement; (5) a pres- sure sensor array operative to generate a plurality of pressure measurements; and (6) a pressure sensor array time domain multiplexed based on each sensor's respective signal quality.

In operation, the control unit is configured to receive data from multiple sources, process it and output waveforms, measurements and telematics. The one or more pressure sensors are adapted to sense pressure when pressed against an artery such as one of the hand arteries, e.g., the radial, ulnar or brachial artery. The display is adapted to display waveforms, measurements (e.g., blood pressure, heart rate, temperature, etc.) and telematics such as battery status. The power source is adapted to provide energy for the various circuits and may comprise a battery (e.g., lithium ion or lithium ion polymer rechargeable battery). The memory function to store program and data. The device 90 may also comprise a photoplethysmography (PPG) sensor for inde- pendent measurement and synchronization of heart rate. The communication module functions to send data over a com- munication link 114 which may comprise a wired or wireless link. In one embodiment, the device transmits data when the link is available either continuously or intermittently, while in other times the device stores the data in volatile or non-volatile (NV) memory.

In one embodiment, the blood pressure measurement device 90 may be connected to the host unit 120. The host device is configured to communicate with the blood pressure measurement device over the link 114 using communication module 124. The control unit 122 is programmed to display information from or relating to measurements obtained (and optionally processed) by blood pressure measurement device 90.

The wearable device of the present invention provides an array of pressure sensors with flexible properties and a biocompatible material interface between the sensors and a user's skin. In one embodiment, the pressure sensor array uses a (i.e. electrically conductive) material such as Velostat or Linqstat electrically conductive film as a substrate and places conductors in a suitable configuration, e.g., in an interdigitated or opposing configuration to form multiple individual sensor elements. A characteristic of the Velostat and Linqstat electrically conductive material is that its resistance is reduced when pressure is applied to it. The array also comprises a mechanical interface placed over the sensor elements to create the sensor array. It is noted this solution is much cheaper, more flexible and has a more comfortable interface to the skin.

A diagram illustrating a side view of a wrist band wear- able in a loose state in accordance with an embodiment of the present invention is shown in FIG. 6. The exploded side view of the wristband wearable, generally referenced 130, includes a housing 134, display 136, wristband 144, and pressure sensor array (i.e. a single sensor, multiple sensors, or force resistive sensing sheet (referred to as "pressure sensor") 142. The device is placed loosely around the user's wrist 138. In this state, the pressure sensor 142 cannot sense the pulsating pressure wave from the artery 132 due to the lack of contact with user's body surface 1408 because wristband 144 is not close enough around the wrist.

A diagram illustrating a side view of a wrist band wear- able in a snug state in accordance with an embodiment of the present invention is shown in FIG. 7. Here, the device 130 is shown with the wristband 144 closed snugly around the user's tubular extremity organ 138. The pressure sensor 142 is not properly situated over the artery 132 and the device is able to measure the user's blood pressure. The wristband 144 configured to be closed around the skin surface 140 of a tubular extremity organ (e.g., finger, wrist, arm, leg, etc.) containing a target blood vessel (e.g., brachial, radial, ulna, femoral, or one of the proper palmar digital arteries) 132, while applying moderate pressure (significantly less than the systolic pressure in the blood vessel 132, but enough to sense the pressure wave). In this state, the pressure sensor 142, located adjacent to pulsating artery 132 on the body surface, can sense the pulsating pressure wave from the artery, due to sufficient contact with body surface 140, because the wrist strap 144 is sufficiently tight around the wrist.

A high level block diagram illustrating an example wear- able measurement device in accordance with the present invention is shown in FIG. 8. The wearable measurement device, generally referenced 151, comprises a pressure sen- sor array 152 incorporating one or more pressure sensor elements 154, processor 150, and display 172. The processor 150 comprises sensor circuit 158 including one or more analog to digital converters (ADCs) 160, and signal proces- sor 164 including pulse analysis block 166. The display 172 comprises a video display for generating images and graphs 174, blood pressure data 175, messages 176, and a place- ment and quality feedback score 178.

In operation, data passing from the pressure sensor 152, applied to a body surface, through single or multiple analog lines 156 to one or more ADCs 160 in sensor circuit 158. In one embodiment, the pressure sensor 152 comprises mul- tiple individual sensing elements 154, hence multiple signals are passed from the pressure sensor to processor 150. The ADCs 160 function to convert the one or more analog signals to corresponding digital signals 162, which are input to processor 164 including a pulse analysis system 166.

The pulse analysis system functions to perform two operations. The first function is to compute from signals 162 a qualitative measure with respect to the quality of the placement and contact of the pressure sensor 152 with body surface 140 (FIG. 7), which is related to the ability to sense the pressure waveform from artery 132. Once the system 166 determines there is proper placement and sufficient contact between the pressure sensor and the body surface, the pulse analysis system 166 calculates a compounded pressure waveform 174 to be displayed on display 172 and/or the systolic and diastolic blood pressure measurement 175. In one embodiment, the display 172 is located on the wristband 144. In another embodiment, the display 172 is located on a mobile phone or tablet device, communicating via wireless communications with the processor 150 on the wristband 144 configured to collect signals from the pres- sure sensor 142.

In another embodiment, the pulse analysis system 166 is operative to compute a continuous metric (or score) related to the quality of placement and contact, where zero repre- sents no discernible contact, and 100 represents optimal contact. In another embodiment, pulse analysis system 166 computes a series of qualitative classes for quality of contact, where zero denotes no discernible proximity, one denotes small proximity, two denotes mild contact, three denotes barely sufficient contact, four denotes good contact, and five denotes optimal contact. Note that any number of classes may be used to delineate the level of contact.

In another embodiment, the pulse analysis system 166 functions to compute a binary metric for the quality of contact, where zero represents insufficient contact for operation, and one represents sufficient contact for operation. In yet another embodiment, the contact quality score is translated to a required number of 'rungs' or 'notches' along the wristband ladder to fasten the wristband tightly enough to get a sufficiently good contact quality reading. The term wristband ladder refers to the 'ladder' shape of wristbands having horizontal slots or openings for the clasp that make the wristband appear as rungs on a ladder. In this embodiment, the device can illuminate (e.g., via LEDs) how much of the wristband needs to be tightened (e.g., how many notches or 'rungs' of the ladder to tighten).

The placement and contact quality metric (i.e. validity score, quality score or simply score) 168 output from the pulse analysis system 166 is displayed via display 172 for the user as a number 178 between zero and one hundred. Note that in one embodiment, a score is provided for each individual sensor in the array. Alternatively, a single combined score is presented representing a weighted combination of all the sensors in the array. In addition, a heat sensor in the wearable device can be used in determining the quality metric (i.e. validity score). Further, a running quality metric or validity score over time can be provided as feedback to the user.

In one embodiment, the methods described herein can be extended so as to average the quality score (per sensor) over a relatively short period of time encompassing several heart beats (e.g. 15 seconds). This yields more robust and higher quality values and reduces the noise and variability of the quality score.

If the score is below a certain threshold, no pulse waveform 174 is displayed on the screen and a message such as "FASTEN WRISTBAND TIGHTER" 176 is displayed to the user. If the score is equal to or above a certain threshold, the pulse waveform 174 and/or systolic and diastolic blood pressure values 175 are displayed on the screen 172.

A high level block diagram illustrating an example signal processor portion of the wearable measurement device of the present invention is shown in FIG. 9. The signal processor 164 comprises a pulse analysis block 166 that includes a blood pressure/pulse detection block 182, an optimize compounded pulse block 184, and a pulse waveform decomposition block 186.

A flow diagram illustrating an example user feedback method in accordance with the present invention is shown in FIG. 10. With reference to FIGS. 9 and 10, in operation, digital data 180 from the sensor circuit 158 (FIG. 8) is received by the pulse analysis block 166 (step 190). The next step in the pulse analysis of digital raw signals 180 is a blood pressure pulse detection mechanism 182 (step 192). In one embodiment, blood pressure detection is applied to all raw signals 180. In an alternative embodiment, blood pressure detection is applied to a subset of signals 180, where the subset is representative of all raw signals.

If no blood pressure signal is detected by blood pressure detection (step 194), the pressure waveform 221, and systolic/diastolic blood pressure data is not displayed. Rather, feedback is provided to the user (step 206). The feedback may take any suitable form such as text messages, non-text messages, lights, visible messages, audible messages, and haptic vibrations. For example, a text message such as "FASTEN WRISTBAND TIGHTER" is displayed on display 172 as text 176 to alert the user to rearrange and/or tighten the device on their wrist. In another embodiment, the placement and contact quality score is displayed as a number 178. Note that the messages may be emphasized by use of larger or bold font, bright color (e.g., red), and/or flickering or flashing to get the user's attention. In another embodiment, the processor 150 emits a unique audible sound to attract the user's attention, and signal them that wristband 144 has poor placement and/or contact with body surface 140.

In the event that blood pressure/pulse was detected (step 194), a quality metric is calculated reflecting a measure of the quality of the placement and contact of the device on the user (step 196). If the quality metric is below a threshold (step 198), negative feedback is provided to the user as described supra (step 206) and the method ends. If the quality metric is above a threshold, then positive feedback is provided to the user (e.g., the score 178 is displayed) (step 199) and the method proceeds with processing the sensor data (step 200). The steps of optimizing the compounded pulse (step 202) and pulse waveform decomposition including systolic blood pressure (SBP) and diastolic blood pressure (DBP) extraction (step 204) are then performed.

The resulting blood pressure waveform 174, and systolic/diastolic blood pressure values 175 are displayed to the user. In one embedment, a placement and contact quality score calculated by the blood pressure detection block 182 is displayed as a number 178. The output of the blood pressure pulse waveform analysis 166 comprises the compounded pulse waveform 174, and SBP/DBP values 175 which are displayed on display 172.

A flow diagram illustrating an example method of searching for a blood pressure/pulse signal in accordance with the present invention is shown in FIG. 11. The blood pressure detection mechanism functions to determine whether an input pressure signal is considered to exhibit a blood pressure pulse. In one embodiment, a binary score is generated but alternatively a general score one through one hundred can also be generated. Note that this method is performed independently on the signal output of each individual sensor element in the pressure sensor array.

First, sensor data is received from a sensor element (step 210). A sliding spectrum estimation is performed on the sensor signal (step 212). Given a signal $x_i$ we take a subset of the signal of length T seconds. Then we calculate the spectrum of the signal defined as follows:

$$X_j = fft(x_i) \tag{1}$$

$$S_j = |X_j^2| \tag{2}$$

where $|v|$ is the magnitude operator of the complex number v. Next, we find the peak, or the maximal value of the spectrum, and check its value:

$$S_{peak} = \max(S_j) \tag{3}$$

$$i_{peak} = \operatorname{argmax}(S_j) \tag{4}$$

The spectrum in a short time window of several seconds is input to the baseline noise removal step which only outputs spectrum that is above a predefined noise threshold level (step 214).

The noise spectrum is removed using a relative threshold $C_{Thr}$ b (e.g., 0.1 of the peak value) we compute the absolute threshold $Thr_S$ and remove all spectrum values lower than it since they are presumed to be noisy spectrum samples.

$$Thr_S = S_{peak} C_{Thr} \qquad (5)$$

$$S_j = \begin{cases} 0 & S_j < Thr_S \\ S_j & S_j \geq Thr_S \end{cases} \qquad (6)$$

Energy normalization is then performed on the clean spectrum such that the sum of all energy levels in different spectral frequency bins is equal to one (step 216). The spectrum is normalized using the following:

$$S_j = \frac{S_j}{\sum S} \qquad (7)$$

The relative energy in a predefined spectral region around an energy peak is calculated (step 218). The peak prominence is checked using a predefined neighborhood around the peak A, and its power is calculated using:

$$P_{peak} = \sum_{i_{peak}-\Delta}^{i_{peak}+\Delta} S_i \qquad (8)$$

The power is then compared to a predefined threshold (step 220). If the peak power $P_{peak}$ is below the threshold then appropriate feedback is provided to the user (step 224). If the peak power $P_{peak}$ is above a valid threshold, the peak is valid and we proceed to analyze it with sensor data processing and pressure pulse waveform analysis in step 202 (FIG. 10) (step 222).

A diagram illustrating an example sensor signal that does not exhibit blood pressure characteristics is shown in FIG. 12. The example graph 246 represents the pressure signal after removing the noise level 248 and normalizing the spectral energy. In this example, the relative energy in a spectral region 244 around spectral peak 240 is below a predefined threshold. Thus, the mechanism of the present invention determines that the input signal does not display blood pressure characteristics. Negative feedback to the user is sent to the display and pressure pulse waveform analysis is not performed.

A diagram illustrating an example sensor signal that exhibits blood pressure characteristics is shown in FIG. 13. The example graph 238 represents the pressure signal after the removal of the noise level 236 and normalizing the spectral energy. In this example, the relative energy in a spectral region 232 around spectral peak 230 is above a predefined threshold. Thus, the mechanism of the present invention determines that the input signal displays blood pressure characteristics. Positive user feedback to the user is sent to the display and pressure pulse waveform analysis is then performed.

As described supra, the method of FIG. 11 is typically applied to a single exemplary signal and is performed over all received digital sensor signals. In another embodiment, the method of FIG. 11 is performed over a subset of received digital sensor signals, whereby they are sampled uniformly based on the spatial arrangement of the sensors that originated the signals.

In another embodiment, the placement and contact score of each signal is multiplied by a weight. The weight being determined by the relative position of the individual sensor in the pressure sensor array. The weighted scores are summed to produce an overall weight of placement and contact quality.

In an alternative embodiment, the weighted scores are compared to generate spatial agreement, such that signals from spatially adjacent signals should produce blood pressure detection scores which are similar to each other within a predefined tolerance. If this condition is not met, poor placement and contact is assumed and negative feedback is provided to the user (step 224, FIG. 11).

The feedback provided by the device can vary depending on the level desired. For example, a simple 'go' or 'no go' signal in the form of an audible beep, light, text messages, non-text messages, visible messages, audible messages, and haptic vibrations can be provided. In one embodiment, more detailed feedback can be provided in the form of directional signals indicating specifically how to reposition the device, whether to tighten the device, etc. to achieve optimum contact between the sensor elements and the user's body. Several examples are provided infra.

In one embodiment, the wearable device also comprises a temperature sensor 69 (FIG. 4) to aid in differentiating between poor signal from the sensor elements due to poor contact of the wristband against the user's skin or misplacement of the wristband above the artery. The temperature sensor may be located, for example, on the inside of the wristband so it can detect skin temperature. When the device is presented with poor signal, the system reads the temperature sensor and if it provides low temperature values, it means the wristband is not tight enough and there is poor contact with the skin. If the sensor measures close to standard human skin temperature, then the cause for poor signal reception is incorrect placement (i.e. anatomical) of the wristband indicating that the pressure sensors are not located optimally above the artery. Note that using a temperature based skin sensor enables the device to provide different feedback to the user, e.g., "FASTEN WRIST-BAND TIGHTER" when low temperature values measured, or "REORIENT SENSOR" when normal body temperature values measured.

In another embodiment, the onboard accelerometer 80 (FIG. 4) can be used to identify the wristband motion and validate that the user is following the feedback instructions. If the user is not following the instructions, further appropriate feedback can be provided to the user. The accelerometer can also be used to detect and identify unwanted movement of the wristband on the arm (e.g., movement and/or rotation out of optimum placement), after the wristband was placed correctly on the wrist. Undesirable movement can be detected and appropriate feedback provided to the user.

A diagram illustrating a first example of sensor contact quality user feedback generated by the present invention is shown in FIG. 14. The example display 250 represents visual representation of the quality metrics associated with each sensor element in an example sensor array comprising 25 sensor elements. The size of each sensor displayed 252 is proportional to the quality metric. Thus, bigger circles represent higher quality metrics for a sensor element than a smaller circle. Ideally, a user places the wearable on their person, e.g., around their wrist, such that the sensor element closest to the center of the array has the largest quality metric. In this example, the sensor array is positioned optimally on the user's wrist. Thus, the largest and brightest circle 254 having the largest quality metric is located in the center.

The examples provided in FIGS. 15, 16, and 17 depict the sensor array positioned non-optimally on the user's wrist. In FIG. 15, the sensor array 260 is positioned such that element 266 generates the largest metric, elements 264 generate somewhat smaller metrics, and the remaining elements 262 receive little to no signal. Thus, by way of the visual display, the device provides directional feedback to the user instructing them to move the device down and to the left so that the elements receiving the strongest blood pressure signal are closer to the center of the array.

In FIG. 16, the sensor array 270 is positioned such that element 276 generates the largest metric, elements 274 generate somewhat smaller metrics, and the remaining elements 272 receive little to no signal. Thus, by way of the visual display, the device provides directional feedback to the user instructing them to move the device upward so that the elements receiving the strongest blood pressure signal are closer to the center of the array.

In FIG. 17, the sensor array 280 is positioned such that element 286 generates the largest metric, elements 284 generate somewhat smaller metrics, and the remaining elements 282 receive little to no signal. Thus, by way of the visual display, the device provides directional feedback to the user instructing them to move the device downward and slightly to the right so that the elements receiving the strongest blood pressure signal are closer to the center of the array.

It is appreciated that the configuration of the individual sensor elements in the sensor array can take numerous shapes. A diagram illustrating a fifth example of sensor contact quality user feedback generated by the present invention is shown in FIG. 18. In this example, the sensor array 360 is two dimensional and comprises a plurality of sensor elements 362 placed diagonally across the array. This configuration is capable of covering device movements incorporating both translation (up or down the wrist) and rotation around the wrist.

A diagram illustrating a sixth example of sensor contact quality user feedback generated by the present invention is shown in FIG. 19. In this example, the sensor array 370 is one dimensional and comprises a plurality of sensor elements 372 placed horizontally across the array.

A diagram illustrating a seventh example of sensor contact quality user feedback generated by the present invention is shown in FIG. 20. In this example, the sensor array 380 is one dimensional and comprises a plurality of sensor elements 382 placed vertically down the array.

Each of the sensor array configurations shown supra have advantages and disadvantages associated with them and may or may not be suitable depending on the particular implementation of the invention.

A flow diagram illustrating a directional user feedback method in accordance with the present invention is shown in FIG. 21. First, the sensor circuit receives an analog signal form each sensor element in the sensor array and digitizes each signal to generate a plurality of digital signals (step 290). The processor then performs pulse waveform analysis on the digitized output of each sensor element (step 292). A quality metric is calculated for each sensor element (step 294). A spatial map of the quality metrics for the entire sensor array is generated (step 296). Directional feedback is generated and provided to the user in accordance with the spatial map of quality metrics, such as shown in FIGS. 14, 15, 16, 17, 18, 19, and 20 described supra (step 298). Optionally, the device provides continuous feedback to the user as the user adjusts the position of the device including the sensor array on their person (step 300). Thus, depending on where the largest valued metrics lie on the sensor array spatial map, the device provides feedback instructions to the user to reposition the device, e.g., upwards, downwards, left, right, clockwise, counterclockwise, etc.

A diagram illustrating an eighth example of sensor contact quality user feedback generated by the present invention is shown in FIG. 22. The example exploded/axial view shown may be easier for a user to interpret the position of the pressure sensor array relative to the artery. This user feedback, however, is only relevant for left/right (i.e. clockwise/ counterclockwise) guidance. A visual indicator such as a sequence of lights or LEDs 324 are placed on the edge portion of wristband 144 or sensor array 142 itself. The visual indicator is configured to illuminate one or more LEDs to indicate the current positioning and placement of the sensor array over the artery. The center LED being the desired one to be lit indicating that the sensor array is optimally positioned (i.e. centered) over the artery. In this example, LED 320 is strongly lit and its adjoining LED to the left 322 is dimly lit while the remaining LEDs are off. This indicates that the placement of the sensor array is too far clockwise and thus needs to be rotated counterclockwise a bit, as indicated by arrow 321.

A diagram illustrating a ninth example of sensor contact quality user feedback generated by the present invention is shown in FIG. 23. In this example, the sequence of LEDs displays different feedback. Here, LED 314 is strongly lit and its adjoining LED to the right 312 is dimly lit while the remaining LEDs are off. This indicates that the placement of the sensor array is too far counterclockwise and thus needs to be rotated clockwise a bit, as indicated by arrow 311.

A diagram illustrating a tenth example of sensor contact quality user feedback generated by the present invention is shown in FIG. 24. In this example user feedback is provided that comprises a four-way directional arrow 358, waveform 354, quality metric or score 352 and blood pressure measurement 356. In operation, the arrows provide feedback regarding the placement and contact quality of the sensor array. If the quality metric exceeds a threshold, no arrows are lit. Otherwise, the arrows indicating the direction the device should be moved and/or rotated to achieve optimal placement and contact are illuminated or blinking. Alternatively, a text message may be displayed conveying the same information. The left/right arrows indicate rotation around the user's write while the up/down arrows indicate translation along the user's wrist. Typically, one or two arrow segments are lit simultaneously to indicate which direction(s) to move the device. Here, the left arrow segment is lit indicated to the user that the device should be rotated in the direction of the arrow to improve the quality metric. In addition, an alphanumeric message can be displayed to the user indicating whether the wristband is too loose and should be tightened. It is noted that directional indications can only be generated from a 2D sensor array, whereas simple contact quality, or a "TIGHTEN WRSTBAND" command can be generated by a single sensor element.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediary components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In the claims, any reference signs placed between parentheses shall not be construed as limiting the claim. The use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first," "second," etc. are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A computer-implemented method of providing feedback to a user relating to proper quality of placement and contact of a blood pressure sensor in a wearable device, the method comprising:

receiving blood pressure waveform data from a blood pressure sensor array comprising a plurality of pressure sensors;

calculating, via a processor housed within the wearable device, individual quality metrics, in accordance with said blood pressure sensor array waveform data, using pulse analysis comprising at least two of: sliding spectrum estimation, normalizing spectral energy, noise level, spectral peak(s) power, pulse decomposition or blood pressure pulse detection, for individual pressure sensors;

generating a spatial map representing the individual quality metrics for the blood pressure sensor array;

calculating, via the processor, a final quality metric as a function of the individual quality metrics and the spatial map, wherein said final quality metric is indicative of proper placement and contact quality;

comparing the final quality metric to a pre-determined threshold score;

providing real-time feedback to the user, if the final quality metric and the spatial map are indicative of inadequate placement and/or contact quality, said feedback comprises instructing the user to adjust the placement and/or contact of the wearable device in at least one of the following directions: clockwise, counterclockwise, upward, or downward, in accordance with the spatial map; and dynamically updating feedback instructions in real time, as the user modifies the placement of the wearable device.

2. The method according to claim 1, wherein said individual quality metrics indicate the quality of the signal and/or whether a pulse was found or not, for the respective pressure sensor of the array.

3. The method according to claim 1, wherein if said final quality metric indicates no pulse found or if the final quality metric is below the threshold score, said feedback indicates action is required by the user before a blood pressure measurement can be made.

4. The method according to claim 1, wherein if said final quality metric indicates no pulse found or if the final quality metric is below the threshold score, said feedback provides the one or more indications to the user regarding proper placement and/or tightness of said wearable device.

5. The method according to claim 1, wherein if said final quality metric indicates a pulse was found or if the final quality metric is above the threshold score, said feedback indicates no action is required.

6. The method according to claim 1, wherein said feedback comprises at least one of text messages, non-text messages, lights, visible messages, audible messages, and haptic vibrations.

7. The method according to claim 1, further comprising presenting the spatial map to a user as a feedback.

8. The method according to claim 1, wherein said feedback further comprises indicating to the user to tighten the wearable device to position a center of the sensor array directly over an artery to be measured.

9. The method according to claim 1, further comprising detecting skin temperature to aid in determining whether said wearable device is incorrectly placed over an artery or not tight enough around a user's wrist.

10. An apparatus for providing feedback to a user relating to proper quality of placement and contact of a blood pressure sensor in a wearable device, comprising:

a wristband for attachment to a user's body;

a pressure sensor array mounted on said wristband, said pressure sensor array comprising a plurality of pressure sensors;

a processor housed within the wearable device, said processor coupled to a memory and operative to:

receive sensor waveform data from said pressure sensor array and calculate a quality metric for individual pressure sensors in said pressure sensor array based on waveform pulse analysis comprising at least two of:

sliding spectrum estimation, normalizing spectral energy, noise level, spectral peak(s) power, pulse decomposition or blood pressure pulse detection;

generate a spatial map representing the individual quality metrics for the entire pressure sensor array;

calculate a final quality metric as a function of the individual quality metrics and the spatial map, said final quality metric is indicative of proper placement and contact quality of said pressure sensor array on the user's body;

compare the final quality metric to a pre-determined threshold score;

generate real-time user feedback based on said final quality metric; and a feedback device coupled to said processor, said feedback device configured to provide feedback instructions to the user, in real time;

wherein if the final quality metric and the spatial map are indicative of inadequate placement and/or contact quality, the feedback comprises one or more-instructions to adjust the placement and/or contact of the wearable device, in at least one of the following directions: clockwise, counterclockwise, upward, or downward, in accordance with the spatial map;

wherein the processor is further configured to dynamically update the feedback, in real time, as the user modifies the placement of the wearable device on his person.

11. The apparatus according to claim 10, wherein the user feedback is selected from at least one of text messages, non-text messages, lights, visible messages, audible messages, and haptic vibrations.

12. The apparatus according to claim 10, wherein said final quality metric calculated by the processor is indicative as to the quality of the pressure signal and/or whether a pulse was detected or not.

13. The apparatus according to claim 10, wherein said processor is operative to present the spatial map to the user as a feedback.

14. The apparatus according to claim 10, wherein said user feedback comprises indicating to the user to at least one of (1) move the wearable device clockwise or counterclockwise along the wrist to position a center of the sensor array directly over an artery to be measured, (2) move the wearable device up or down the arm to position a center of the sensor array directly over an artery to be measured, and (3) tighten the wearable device to position a center of the sensor array directly over an artery to be measured.

15. The apparatus according to claim 10, further comprising a temperature sensor adapted to detect skin temperature to aid in determining whether said wearable device is incorrectly placed over an artery or not tight enough around a user's wrist.

16. A wearable device for measuring blood pressure of a user, comprising:

a wristband for attachment to a user's body;

a housing mounted on said wristband;

a display mounted in said housing for displaying blood pressure data;

a pressure sensor array mounted on said wristband, said pressure sensor array comprising a plurality of pressure sensors and operative to acquire a blood pressure waveform signal;

a processor housed within the housing and coupled to a memory, said processor operative to receive sensor waveform data from said pressure sensor array and calculate a quality metric for individual pressure sensors in said pressure sensor array, using pulse analysis comprising at least two of: sliding spectrum estimation, normalizing spectral energy, noise level, spectral peak(s) power, pulse decomposition or blood pressure pulse detection;

generate a spatial map representative of the individual quality metrics for the entire pressure sensor array;

calculate a final quality metric as a function of the individual quality metrics and the spatial map, said quality metric is indicative of proper placement and contact quality of said pressure sensor array on the user's person, wherein the final quality metric indicates the quality of the pressure signal;

compare the final quality metric to a pre-determined threshold score;

generate real-time user feedback based on said quality metric;

if said final quality metric exceeds a threshold, generate a blood pressure measurement for indicating on said display; and a feedback device coupled to said processor, said feedback device configured to provide feedback instructions to the user, in real-time, wherein if the final quality metric and the spatial map are indicative of inadequate placement and/or contact quality, the feedback comprises one or more instructions to adjust the placement and/or contact of the wearable device, in at least one of the following directions: clockwise, counterclockwise, upward, or downward, in accordance with the spatial map;

wherein the processor is further configured to dynamically update the feedback as the user modifies the placement of the wearable device on his person.

17. The wearable device according to claim 16, wherein said user feedback comprises at least one of text messages, non-text messages, lights, visible messages, audible messages, and haptic vibrations as user feedback.

18. The wearable device according to claim 16, wherein said user feedback comprises indicating to the user to at least one of (1) move the wearable device clockwise or counterclockwise along the wrist to position a center of the sensor array directly over an artery to be measured, (2) move the wearable device up or down the arm to position a center of the sensor array directly over an artery to be measured, and (3) tighten the wearable device to position a center of the sensor array directly over an artery to be measured.

19. The wearable device according to claim 16, further comprising a temperature sensor adapted to detect skin temperature to aid in determining whether said wearable device is incorrectly placed over an artery or not tight enough around a user's wrist.

* * * * *